(12) United States Patent
Antoine et al.

(10) Patent No.: US 8,748,109 B2
(45) Date of Patent: Jun. 10, 2014

(54) METHOD FOR THE DETECTION OF ORGAN OR TISSUE INJURY

(75) Inventors: Daniel Antoine, Liverpool (GB); Dominic Williams, Liverpool (GB); Kevin Park, Liverpool (GB)

(73) Assignee: The University of Liverpool, Liverpool (GB)

( * ) Notice: Subject to any disclaimer, the term of this patent is extended or adjusted under 35 U.S.C. 154(b) by 25 days.

(21) Appl. No.: 13/381,238

(22) PCT Filed: Jul. 5, 2010

(86) PCT No.: PCT/GB2010/051107
§ 371 (c)(1),
(2), (4) Date: Dec. 28, 2011

(87) PCT Pub. No.: WO2011/001191
PCT Pub. Date: Jan. 6, 2011

(65) Prior Publication Data
US 2012/0107832 A1    May 3, 2012

(30) Foreign Application Priority Data
Jul. 3, 2009   (GB) .................................. 0911569.2

(51) Int. Cl.
*G01N 33/53*    (2006.01)

(52) U.S. Cl.
USPC .......................................... 435/7.1; 436/518

(58) Field of Classification Search
None
See application file for complete search history.

(56) References Cited

U.S. PATENT DOCUMENTS

| 8,361,723 | B2* | 1/2013 | Omary et al. ................. 435/6.11 |
| 2004/0219633 | A1 | 11/2004 | Bolhuis et al. |
| 2006/0111287 | A1 | 5/2006 | Bianchi |
| 2008/0081348 | A1 | 4/2008 | Feldstein et al. |
| 2009/0054741 | A1* | 2/2009 | McAleer ........................ 600/301 |
| 2009/0098104 | A1 | 4/2009 | Ankersmit |
| 2009/0221004 | A1* | 9/2009 | Hong ........................... 435/7.23 |
| 2010/0248261 | A1* | 9/2010 | Ranish et al. ................... 435/7.1 |
| 2012/0201819 | A1* | 8/2012 | Liu et al. ..................... 424/134.1 |

FOREIGN PATENT DOCUMENTS

| WO | WO 2004044001 | * | 5/2004 |
| WO | WO2008/079269 | | 7/2008 |

OTHER PUBLICATIONS

PCT International Search Report and Written Opinion for PCT/GB2010/051107, prepared Sep. 24, 2010.
United Kingdom Search Report and Written Opinion for GB0911569.2, prepared Nov. 4, 2009.

* cited by examiner

*Primary Examiner* — Jacob Cheu
(74) *Attorney, Agent, or Firm* — Barnes & Thornburg LLP

(57) ABSTRACT

This invention relates to methodology for detecting, assessing and/or diagnosing the presence of organ or tissue injury. More specifically, the present invention relates to methodology for detecting particular serum biomarkers that can be used in the detection, assessment and/or diagnosis of organ (e.g. liver) or tissue (e.g. skin) injury.

14 Claims, 7 Drawing Sheets

SEQUENCE LISTING

```
<160> NUMBER OF SEQ ID NOS: 15

<210> SEQ ID NO 1
<211> LENGTH: 430
<212> TYPE: PRT
<213> ORGANISM: Homo sapiens

<400> SEQUENCE: 1

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125
```

Tyr Phe Lys Ile Ile Glu Asp Leu Arg Ala Gln Ile Phe Ala Asn Thr
            130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
                180                 185                 190

Asn Ile Thr Arg Leu Gln Leu Glu Thr Glu Ile Glu Ala Leu Lys Glu
            195                 200                 205

Glu Leu Leu Phe Met Lys Lys Asn His Glu Glu Val Lys Gly Leu
            210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
                260                 265                 270

Gln Gln Ile Glu Glu Ser Thr Thr Val Val Thr Thr Gln Ser Ala Glu
            275                 280                 285

Val Gly Ala Ala Glu Thr Thr Leu Thr Glu Leu Arg Arg Thr Val Gln
290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
            355                 360                 365

Ile Lys Val Lys Leu Glu Ala Glu Ile Ala Thr Tyr Arg Arg Leu Leu
            370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
                420                 425                 430

<210> SEQ ID NO 2
<211> LENGTH: 423
<212> TYPE: PRT
<213> ORGANISM: Mus musculus

<400> SEQUENCE: 2

Met Ser Phe Thr Thr Arg Ser Thr Thr Phe Ser Thr Asn Tyr Arg Ser
1               5                   10                  15

Leu Gly Ser Val Arg Thr Pro Ser Gln Arg Val Arg Pro Ala Ser Ser
            20                  25                  30

Ala Ala Ser Val Tyr Ala Gly Ala Gly Gly Ser Gly Ser Arg Ile Ser
        35                  40                  45

Val Ser Arg Ser Val Trp Gly Gly Ser Val Gly Ser Ala Gly Leu Ala
    50                  55                  60

Gly Met Gly Gly Ile Gln Thr Glu Lys Glu Thr Met Gln Asp Leu Asn
65                  70                  75                  80

```
Asp Arg Leu Ala Ser Tyr Leu Asp Lys Val Lys Ser Leu Glu Thr Glu
                85                  90                  95

Asn Arg Arg Leu Glu Ser Lys Ile Arg Glu His Leu Glu Lys Lys Gly
                100                 105                 110

Pro Gln Gly Val Arg Asp Trp Gly His Tyr Phe Lys Ile Ile Glu Asp
                115                 120                 125

Leu Arg Ala Gln Ile Phe Ala Asn Ser Val Asp Asn Ala Arg Ile Val
            130                 135                 140

Leu Gln Ile Asp Asn Ala Arg Leu Ala Ala Asp Asp Phe Arg Val Lys
145                 150                 155                 160

Tyr Glu Thr Glu Leu Ala Met Arg Gln Ser Val Glu Ser Asp Ile His
                165                 170                 175

Gly Leu Arg Lys Val Val Asp Asp Thr Asn Ile Thr Arg Leu Gln Leu
                180                 185                 190

Glu Thr Glu Ile Glu Ala Leu Lys Glu Glu Leu Leu Phe Met Lys Lys
                195                 200                 205

Asn His Glu Glu Glu Val Gln Gly Leu Glu Ala Gln Ile Ala Ser Ser
                210                 215                 220

Gly Leu Thr Val Glu Val Asp Ala Pro Lys Ser Gln Asp Leu Ser Lys
225                 230                 235                 240

Ile Met Ala Asp Ile Arg Ala Gln Tyr Glu Ala Leu Ala Gln Lys Asn
                245                 250                 255

Arg Glu Glu Leu Asp Lys Tyr Trp Ser Gln Gln Ile Glu Glu Ser Thr
                260                 265                 270

Thr Val Val Thr Thr Lys Ser Ala Glu Ile Arg Asp Ala Glu Thr Thr
                275                 280                 285

Leu Thr Glu Leu Arg Arg Thr Leu Gln Thr Leu Glu Ile Asp Leu Asp
                290                 295                 300

Ser Met Lys Asn Gln Asn Ile Asn Leu Glu Asn Ser Leu Gly Asp Val
305                 310                 315                 320

Glu Ala Arg Tyr Lys Ala Gln Met Glu Gln Leu Asn Gly Val Leu Leu
                325                 330                 335

His Leu Glu Ser Glu Leu Ala Gln Thr Arg Ala Glu Gly Gln Arg Gln
                340                 345                 350

Ala Gln Glu Tyr Glu Ala Leu Leu Asn Ile Lys Val Lys Leu Glu Ala
                355                 360                 365

Glu Ile Ala Thr Tyr Arg Arg Leu Leu Glu Asp Gly Glu Asp Phe Ser
                370                 375                 380

Leu Asn Asp Ala Leu Asp Ser Ser Asn Ser Met Gln Thr Val Gln Lys
385                 390                 395                 400

Thr Thr Thr Arg Lys Ile Val Asp Gly Arg Val Val Ser Glu Thr Asn
                405                 410                 415

Asp Thr Arg Val Leu Arg His
                420

<210> SEQ ID NO 3
<211> LENGTH: 423
<212> TYPE: PRT
<213> ORGANISM: Rattus norvegicus

<400> SEQUENCE: 3

Met Ser Phe Thr Thr Arg Ser Thr Phe Ser Thr Asn Tyr Arg Ser
1               5                   10                  15

Leu Gly Ser Val Arg Thr Pro Ser Gln Arg Val Arg Pro Ala Ser Ser
                20                  25                  30
```

Ala Ala Ser Val Tyr Ala Gly Ala Gly Ser Gly Ser Arg Ile Ser
         35                  40                  45

Val Ser Arg Ser Val Trp Gly Ser Val Gly Ser Ala Gly Leu Ala
     50                  55                  60

Gly Met Gly Gly Val Gln Thr Glu Lys Glu Thr Met Gln Asp Leu Asn
 65                  70                  75                  80

Asp Arg Leu Ala Ser Tyr Leu Asp Lys Val Lys Asn Leu Glu Thr Glu
                 85                  90                  95

Asn Arg Arg Leu Glu Ser Lys Ile Arg Glu Tyr Leu Glu Lys Arg Gly
                100                 105                 110

Pro Gln Gly Val Arg Asp Trp Gly His Tyr Phe Lys Thr Ile Glu Asp
                115                 120                 125

Leu Arg Ala Gln Ile Phe Ala Asn Ser Val Asp Asn Ala Arg Ile Val
        130                 135                 140

Leu Gln Ile Asp Asn Ala Arg Leu Ala Ala Asp Asp Phe Arg Val Lys
145                 150                 155                 160

Tyr Glu Thr Glu Leu Ala Met Arg Gln Ser Val Ser Asp Ile His
                165                 170                 175

Gly Leu Arg Lys Val Val Asp Asp Thr Asn Ile Thr Arg Leu Gln Leu
                180                 185                 190

Glu Thr Glu Ile Glu Ala Leu Lys Glu Glu Leu Leu Phe Met Lys Lys
        195                 200                 205

Asn His Glu Glu Glu Val Gln Gly Leu Glu Ala Gln Ile Ala Ser Ser
210                 215                 220

Gly Leu Thr Val Glu Val Asp Ala Pro Lys Ser Gln Asp Leu Ser Lys
225                 230                 235                 240

Ile Met Ala Asp Ile Arg Ala Gln Tyr Glu Gln Leu Ala Gln Lys Asn
                245                 250                 255

Arg Glu Glu Leu Asp Lys Tyr Trp Ser Gln Gln Ile Glu Glu Ser Thr
        260                 265                 270

Thr Val Val Thr Thr Lys Ser Ala Glu Ile Arg Asp Ala Glu Thr Thr
        275                 280                 285

Leu Leu Glu Leu Arg Arg Thr Leu Gln Thr Leu Glu Ile Asp Leu Asp
        290                 295                 300

Ser Met Lys Asn Gln Asn Ile Asn Leu Glu Asn Asn Leu Gly Glu Val
305                 310                 315                 320

Glu Ala Arg Tyr Arg Val Gln Met Glu Gln Leu Asn Gly Val Leu Leu
                325                 330                 335

His Leu Glu Ser Glu Leu Ala Gln Thr Arg Ala Glu Gly Gln Arg Gln
                340                 345                 350

Thr Gln Glu Tyr Glu Ala Leu Leu Asn Ile Lys Val Lys Leu Glu Ala
                355                 360                 365

Glu Ile Ala Thr Tyr Arg Arg Leu Leu Glu Asp Gly Asp Asp Phe Ser
        370                 375                 380

Leu Asn Asp Ala Leu Asp Ser Ser Asn Ser Met Gln Thr Val Gln Arg
385                 390                 395                 400

Thr Thr Thr Arg Lys Val Val Asp Gly Lys Val Val Ser Glu Thr Asn
                405                 410                 415

Asp Thr Arg Val Leu Arg His
                420

<210> SEQ ID NO 4
<211> LENGTH: 25
<212> TYPE: PRT

<213> ORGANISM: Homo sapiens

<400> SEQUENCE: 4

Leu Leu Glu Asp Gly Glu Asp Phe Asn Leu Gly Asp Ala Leu Asp Ser
1               5                   10                  15

Ser Asn Ser Met Gln Thr Ile Gln Lys
            20                  25

<210> SEQ ID NO 5
<211> LENGTH: 25
<212> TYPE: PRT
<213> ORGANISM: Mus musculus

<400> SEQUENCE: 5

Leu Leu Glu Asp Gly Glu Asp Phe Ser Leu Asn Asp Ala Leu Asp Ser
1               5                   10                  15

Ser Asn Ser Met Gln Thr Val Gln Lys
            20                  25

<210> SEQ ID NO 6
<211> LENGTH: 25
<212> TYPE: PRT
<213> ORGANISM: Rattus norvegicus

<400> SEQUENCE: 6

Leu Leu Glu Asp Gly Asp Asp Phe Ser Leu Asn Asp Ala Leu Asp Ser
1               5                   10                  15

Ser Asn Ser Met Gln Thr Val Gln Arg
            20                  25

<210> SEQ ID NO 7
<211> LENGTH: 15
<212> TYPE: PRT
<213> ORGANISM: Homo sapiens

<400> SEQUENCE: 7

Leu Leu Glu Asp Gly Glu Asp Phe Asn Leu Gly Asp Ala Leu Asp
1               5                   10                  15

<210> SEQ ID NO 8
<211> LENGTH: 15
<212> TYPE: PRT
<213> ORGANISM: Mus musculus

<400> SEQUENCE: 8

Leu Leu Glu Asp Gly Asp Phe Ser Leu Asn Asp Ala Leu Asp
1               5                   10                  15

<210> SEQ ID NO 9
<211> LENGTH: 15
<212> TYPE: PRT
<213> ORGANISM: Rattus norvegicus

<400> SEQUENCE: 9

Leu Leu Glu Asp Gly Asp Asp Phe Ser Leu Asn Asp Ala Leu Asp
1               5                   10                  15

<210> SEQ ID NO 10
<211> LENGTH: 215
<212> TYPE: PRT
<213> ORGANISM: Homo sapiens

<400> SEQUENCE: 10

Met Gly Lys Gly Asp Pro Lys Lys Pro Arg Gly Lys Met Ser Ser Tyr

```
              1               5                  10                 15
Ala Phe Phe Val Gln Thr Cys Arg Glu Glu His Lys Lys Lys His Pro
                20                 25                 30

Asp Ala Ser Val Asn Phe Ser Glu Phe Ser Lys Lys Cys Ser Glu Arg
            35                 40                 45

Trp Lys Thr Met Ser Ala Lys Glu Lys Gly Lys Phe Glu Asp Met Ala
        50                 55                 60

Lys Ala Asp Lys Ala Arg Tyr Glu Arg Glu Met Lys Thr Tyr Ile Pro
65                  70                 75                 80

Pro Lys Gly Glu Thr Lys Lys Phe Lys Asp Pro Asn Ala Pro Lys
                85                 90                 95

Arg Pro Pro Ser Ala Phe Phe Leu Phe Cys Ser Glu Tyr Arg Pro Lys
                100                105                110

Ile Lys Gly Glu His Pro Gly Leu Ser Ile Gly Asp Val Ala Lys Lys
            115                120                125

Leu Gly Glu Met Trp Asn Asn Thr Ala Ala Asp Asp Lys Gln His Tyr
        130                135                140

Glu Lys Lys Ala Ala Lys Leu Lys Glu Lys Tyr Glu Lys Asp Ile Ala
145                 150                155                160

Ala Tyr Arg Ala Lys Gly Lys Pro Asp Ala Ala Lys Lys Gly Val Val
                165                170                175

Lys Ala Glu Lys Ser Lys Lys Lys Glu Glu Glu Asp Glu Glu
                180                185                190

Asp Glu Glu Asp Glu Glu Glu Asp Glu Glu Asp Glu Asp Glu
            195                200                205

Glu Glu Asp Asp Asp Asp Glu
        210                215

<210> SEQ ID NO 11
<211> LENGTH: 215
<212> TYPE: PRT
<213> ORGANISM: Mus musculus

<400> SEQUENCE: 11

Met Gly Lys Gly Asp Pro Lys Lys Pro Arg Gly Lys Met Ser Ser Tyr
1               5                  10                 15

Ala Phe Phe Val Gln Thr Cys Arg Glu Glu His Lys Lys Lys His Pro
                20                 25                 30

Asp Ala Ser Val Asn Phe Ser Glu Phe Ser Lys Lys Cys Ser Glu Arg
            35                 40                 45

Trp Lys Thr Met Ser Ala Lys Glu Lys Gly Lys Phe Glu Asp Met Ala
        50                 55                 60

Lys Ala Asp Lys Ala Arg Tyr Glu Arg Glu Met Lys Thr Tyr Ile Pro
65                  70                 75                 80

Pro Lys Gly Glu Thr Lys Lys Phe Lys Asp Pro Asn Ala Pro Lys
                85                 90                 95

Arg Pro Pro Ser Ala Phe Phe Leu Phe Cys Ser Glu Tyr Arg Pro Lys
                100                105                110

Ile Lys Gly Glu His Pro Gly Leu Ser Ile Gly Asp Val Ala Lys Lys
            115                120                125

Leu Gly Glu Met Trp Asn Asn Thr Ala Ala Asp Asp Lys Gln Pro Tyr
        130                135                140

Glu Lys Lys Ala Ala Lys Leu Lys Glu Lys Tyr Glu Lys Asp Ile Ala
145                 150                155                160

Ala Tyr Arg Ala Lys Gly Lys Pro Asp Ala Ala Lys Lys Gly Val Val
```

```
                          165                 170                 175
Lys Ala Glu Lys Ser Lys Lys Lys Glu Glu Glu Glu Asp Glu
                180                 185                 190

Asp Glu Glu Asp Glu Glu Glu Glu Asp Glu Glu Asp Glu Asp Glu
            195                 200                 205

Glu Glu Asp Asp Asp Asp Glu
        210                 215

<210> SEQ ID NO 12
<211> LENGTH: 215
<212> TYPE: PRT
<213> ORGANISM: Rattus norvegicus

<400> SEQUENCE: 12

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 13
<211> LENGTH: 9
<212> TYPE: PRT
<213> ORGANISM: Homo sapiens

<400> SEQUENCE: 13

Lys Ser Lys Lys Lys Lys Glu Glu Glu
1               5

<210> SEQ ID NO 14
<211> LENGTH: 9
<212> TYPE: PRT
<213> ORGANISM: Mus musculus

<400> SEQUENCE: 14
```

```
Lys Ser Lys Lys Lys Lys Glu Glu Glu
1               5

<210> SEQ ID NO 15
<211> LENGTH: 9
<212> TYPE: PRT
<213> ORGANISM: Rattus norvegicus

<400> SEQUENCE: 15

Lys Ser Lys Lys Lys Lys Glu Glu Glu
1               5
```

METHOD FOR THE DETECTION OF ORGAN OR TISSUE INJURY

CROSS-REFERENCE TO RELATED APPLICATIONS

Figure 1:
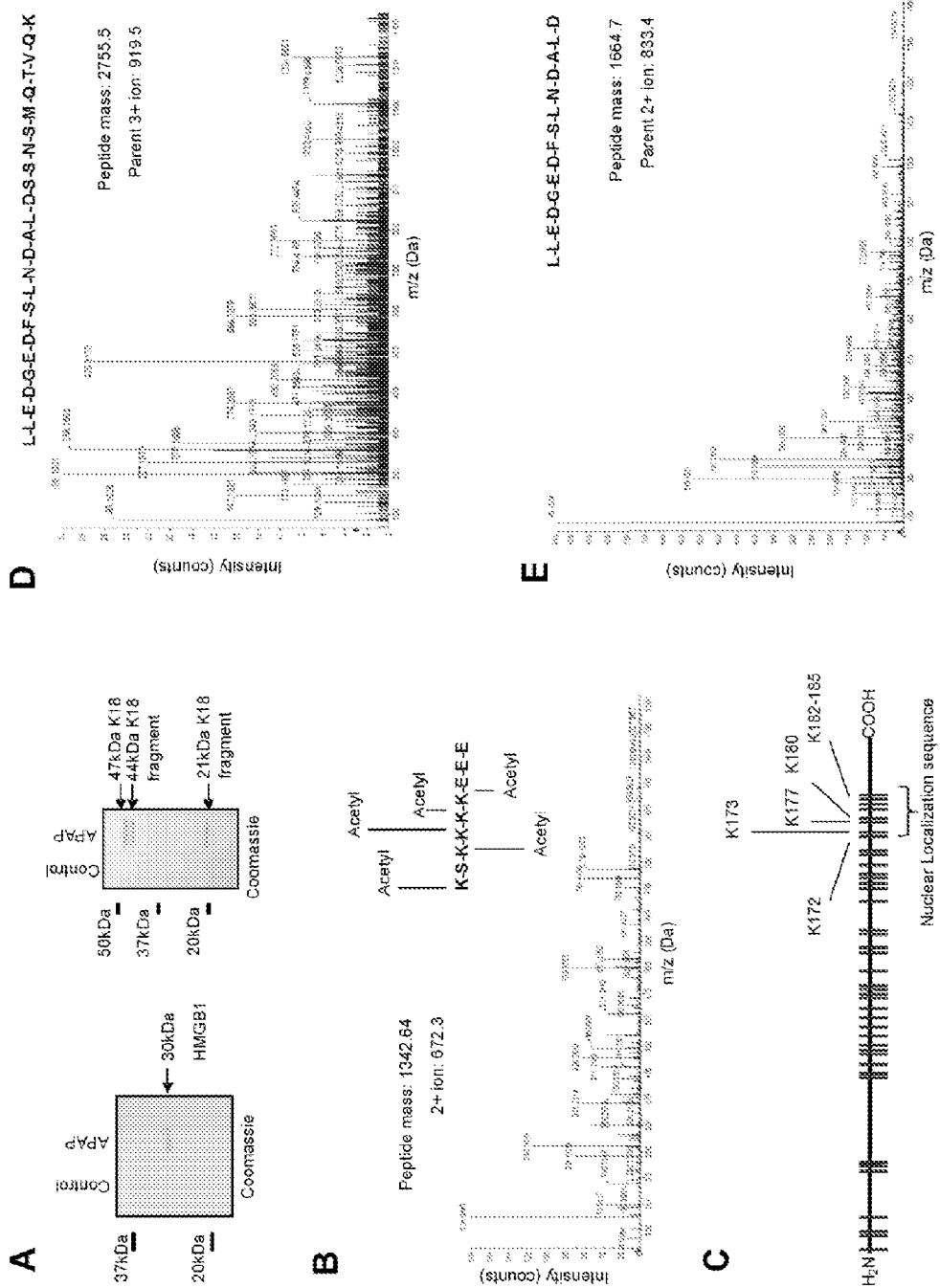

This application is a U.S. national counterpart application of PCT International Application Serial No. PCT/GB2010/051107, filed Jul. 5, 2010, which claims priority to United Kingdom Patent Application Serial Number 0911569.2, filed Jul. 3, 2009, the disclosures of both which are hereby incorporated herein by reference.

This invention relates to a method for the detection, assessment, and/or diagnosis of organ or tissue injury. More specifically, the present invention relates to methodology for detecting particular serum biomarkers that can be used in the detection, assessment and/or diagnosis of drug induced organ or tissue injury.

BACKGROUND

In the pharmaceutical field, adverse drug reactions (ADRs) are a major clinical concern and are a significant cause of attrition in drug development.

Hepatotoxicity is a particularly prominent cause of drug attrition (1, 2). The metabolism of drugs to chemically reactive metabolites in the liver is an important factor in drug-induced liver injury (DILI) (3, 4). However, the cellular events that link the chemistry of drug bioactivation to the toxicological outcome are poorly understood. A better understanding of the mechanisms and pathways leading to DILI would improve clinical management and inform the design of safer medicines for use in the clinic.

In addition, many drugs can also be toxic to other organs and tissues, such as the skin (irritation, rashes etc.), lungs, kidneys and heart. In severe cases, this may lead to drug attrition or necessitate additional clinical management. A better understanding of the mechanisms and pathways leading to skin, lung, kidney and cardiac toxicity would also be beneficial.

The importance of biomarkers to accelerate the pace of drug development, reduce attrition and to be biologically informative in their own right is becoming generally acknowledged in the pharmaceutical field. The ability to easily detect selective biomarkers of apoptosis, necrosis and inflammation would have immense benefit for differentiating the underlying causes of organ injury, such as drug induced liver, skin, lung, kidney or cardiac injury, and will provide additional information to aid clinical intervention and to inform the development of safer drugs in the future.

There are a few biomarkers that are associated with organ injury, such as, for example, alanine aminotransaminase (ALT), which is associated with liver injury. However, the detection of these biomarkers does not reveal any information about the underlying mechanism or progression of the organ damage.

Accordingly, it is an object of the present invention to provide a simple and convenient approach for detecting and/or assessing drug induced organ or tissue injury, which is also sufficiently sensitive so as to enable the early detection of organ or tissue damage.

It is a further object to provide methodology that enables the underlying mechanisms and pathways contributing to drug-induced organ or tissue injury to be assessed.

BRIEF SUMMARY OF THE DISCLOSURE

The present invention resides in the ability to conveniently and non-invasively detect particular serum biomarkers of apoptosis, necrosis and inflammation. The ability to detect all of these serum biomarkers together, and correlate their detection with drug-induced toxicity occurring in a particular organ or tissue, enables an evaluation of the underlying mechanisms and pathways involved in the injury process.

Organ and tissue damage caused by drugs may involve one or more of the processes of apoptosis, necrosis and inflammation. The ability to assess which underlying processes are occurring and the relative contribution of each process enables a better understanding of the nature and stage of the organ or tissue injury that is occurring. It also enables opportunities for targeted clinical intervention to limit the extent of the injury or damage occurring. Furthermore, by monitoring these biomarkers over time, the progression of the organ or tissue injury can be monitored.

The ability to detect and/or assess organ or tissue damage in this way will also be extremely useful in the toxicological screening of potential new therapeutic agents.

Thus, the present invention provides a method of detecting and assessing drug induced apoptosis, necrosis and/or inflammation in a human or animal subject, which comprises testing a serum sample obtained from said subject for:
  i. a specific serum biomarker of apoptosis;
  ii. a specific serum biomarker of necrosis; and
  iii. a specific serum biomarker of inflammation.

The present invention also provides a method of detecting, assessing and/or diagnosing drug induced organ or tissue damage which comprises testing a serum sample to determine the presence of:
  (i) a specific serum biomarker of apoptosis;
  (ii) a specific serum biomarker of necrosis;
  (iii) a specific serum biomarker of inflammation; and
  correlating the presence of one or more of said serum biomarkers with an organ or tissue specific indicator of damage.

In a further aspect, the present invention provides a method of detecting and/or assessing the presence of drug induced apoptosis, necrosis and inflammation associated with an organ or tissue, which comprises testing a serum sample to determine the presence of:
  (i) a specific serum biomarker of apoptosis;
  (ii) a specific serum biomarker of necrosis;
  (iii) a specific serum biomarker of inflammation; and
  correlating the presence of one or more of said serum biomarkers with an organ or tissue specific indicator of damage.

In yet another aspect, the present invention provides a method of monitoring the pathogenesis of organ or tissue damage caused by the administration of a drug to a human or animal subject, said method comprising testing a serum sample from said subject to determine the presence of:
  (i) a specific serum biomarker of apoptosis;
  (ii) a specific serum biomarker of necrosis; and
  (iii) a specific serum biomarker of inflammation; and
  correlating the presence of one or more of said serum biomarkers with an organ or tissue specific indicator of damage.

In a further aspect, the present invention provides an assay for detecting and/or assessing drug-induced organ or tissue damage, said assay comprising:
  means for detecting a specific serum biomarker of apoptosis;
  means for detecting a specific serum biomarker of necrosis; and
  means for detecting a specific serum biomarker of inflammation.

In a further aspect, the present invention also provides kits for detecting, assessing and/or diagnosing organ injury, as defined further herein.

DETAILED DESCRIPTION

The present invention resides in the ability to detect the presence of serum biomarkers of apoptosis, necrosis and/or inflammation. This is achieved by testing a serum sample obtained from a human or animal subject for:

(i) a specific serum biomarker of apoptosis;
(ii) a specific serum biomarker of necrosis; and
(iii) a specific serum biomarker of inflammation.

The serum sample required to carry out the methods of the present invention defined herein is obtained from a human or animal subject using conventional techniques known in the art. The human or animal subject may be a subject that is suspected of having organ or tissue damage, or one that requires monitoring in order to determine whether organ or tissue damage is occurring.

The methods of the present invention are suitably non-invasive. By "non-invasive" we mean that they are practiced outside of the human or animal body on serum samples obtained from the human or animal subject, i.e. the methods are not practiced directly on the human or animal body.

Serum Biomarkers (i) Keratin 18

Keratins are intermediate filament proteins expressed by epithelial cells responsible for cell structure and integrity. Phosphorylation of key serine residues within Keratin-18 (K18) occurs early in Fas-mediated apoptosis (12). Caspase mediated cleavage of K18 is also an early event in the cellular structural rearrangement during apoptosis (13). Caspases 3, 7 and 9 have been implicated in the cleavage of K18 at the C terminal DALD/S motif and caspase 6 has been shown to cleave at the VEVD/A motif within the L1-2 linker region. Full length K18 released passively during necrotic cell death and fragmented K18 generated during apoptosis can be released into the blood and accumulate over time (14). Antibodies have been raised against apoptosis related forms of K18 for investigation in in vivo and clinical situations (15, 16). Serum quantification of caspase-cleaved K18 and full length K18 have been used as markers of apoptosis and necrosis respectively during pharmacodynamic therapeutic drug monitoring in patients of chemotherapeutic agents in the clinic and animal models (17), and for the quantification of apoptosis during liver disorders such as non-alcoholic steatohepatitis (NASH) (18) and hepatitis C infection (19).

By full length K18 we mean the full length K18 protein and/or K18 that has not been subject to caspase-cleavage.

In a particular embodiment of the present invention, caspase-cleaved K18 is utilised as a specific serum biomarker of drug induced apoptosis. For the avoidance of doubt, by caspase-cleaved K18, we mean K18 protein which has been cleaved by a caspase enzyme. As indicated above, the caspase enzymes will cleave K18 at the DALD/S motif or the VEVD/A motif.

In a further embodiment, full length K18, which is passively released during necrotic cell death, is utilised as a serum biomarker of necrosis. For the avoidance of doubt, by full length K18, we mean K18 protein which has not been cleaved by a caspase enzyme (at the DALD/S motif and/or the VEVD/A motif).

The sequences for the full length K18 protein in the human, mouse and rat species are shown in SEQ ID NO.s 1, 2 and 3 respectively.

Full length K18 and caspase-cleaved K18 may be detected by any suitable techniques known in the art. For example, both of these biomarkers may be detected by immunologically based assays (such as ELISA and the immunoassays disclosed in U.S. Pat. No. 6,292,850, U.S. Pat. No. 6,716,968 and U.S. Pat. No. 6,706,488), mass-spectrometry techniques (which can detect the difference in mass between full length and caspase-cleaved K18 fragments) and HPLC techniques.

In an embodiment of the invention, caspase-cleaved K18 and full length K18 are detected and quantified using immunological based assays, especially an ELISA. ELISAs are well known and established techniques for detecting protein biomarkers.

In an alternative embodiment, both caspase-cleaved K18 and/or full length K18 can be conveniently detected and quantified using LC-MS/MS analysis.

To facilitate LC-MS/MS detection and analysis of caspase-cleaved K18 and full length K18, it is desirable to partially digest the serum K18 into fragments using a suitable protease enzyme.

Suitably, one of the peptide fragments formed by the partial digestion of the K18 protein spans one of the caspase cleavage motifs. Any suitable protease enzyme could be used for this purpose and person skilled in art will be able to select a suitable enzyme, or mixture of enzymes, that would generate suitable fragments for mass spectrometry detection.

It is important that one of the fragments generated by the partial digestion of K18 spans one of the caspase cleavage motifs because this enables the fragments in which the caspase cleavage motif is intact (i.e. the full length K18 released during necrosis) and the corresponding fragments that have been subject to caspase cleavage (i.e. the fragment associated with apoptosis) to be detected and differentiated by mass spectrometry.

In a particular embodiment, the peptide fragment formed spans the cleavage site for caspases 3, 7 and 9 (i.e. the DALD/S motif).

In a specific embodiment of the invention, the protease used to partially digest the K18 protein is trypsin, which cleaves peptide linkages at the carboxyl side of the amino acids lysine or arginine.

The full length K18 fragments formed by partially digesting serum K18 with trypsin, and which span the DALD/S cleavage motif targeted by caspases 3, 7 and 9, are shown in SEQ ID NO.s 4 (human), 5 (mouse) and 6 (rat). These fragments can be detected by mass spectrometry.

When the caspase cleaved K18 fragments are digested with trypsin, the fragments shown in SEQ ID NO.s 7 (human), 8 (mouse) and 9 (rat) are formed. These fragments can be detected by mass spectrometry.

Synthetic K18 peptide fragments are commercially available can be used as standards to calibrate the peak intensity observed in the mass spectrometer when they are spiked in control K18 free serum from the species under detection. This enables the amount of the respective serum K18 fragments to be quantified by comparing the peak intensities and area under curve obtained with calibration intensities obtained using the synthetic peptide fragments.

Using mass spectrometry enables the presence of these two K18 biomarkers to be easily determined in a serum sample. Furthermore, the data can be generated in a single assay.

(ii) High Mobility Group Box 1

Recent evidence suggests a key role is played by high mobility group box protein 1 (HMGB-1) in alerting the immune system to dying cells (20, 21). HMGB-1 is a nuclear binding protein that has pro-inflammatory activity and targets Toll-like receptors (TLR) and the receptor for advanced glycation end products (RAGE) on target cells (22, 23). It is released in a hyper-acetylated form on distinct lysine residues from activated innate immune cells (24) and passively in a hypo-acetylated form by necrotic cells, while it is thought not to be released by apoptotic or secondary necrotic cells (21). Anti-HMGB-1 antibodies inhibit the inflammatory response associated with APAP hepatotoxicity and endotoxin lethality in vivo (21, 25).

In a particular embodiment of the invention, the hypo-acetylated form of HMGB-1 is detected as a specific serum biomarker of necrosis.

In a further embodiment, the hyper-acetylated form of HMGB-1 is the specific serum biomarker of inflammation.

Both the hypo-acetylated and hyper-acetylated forms of HMGB-1, released by necrotic and innate immune cells respectively, may be detected by any suitable techniques known in the art. For example, both of these biomarkers may be detected by immunologically based assays (such as ELISA and other immunoassays such as those disclosed in U.S. Pat. No. 6,292,850, U.S. Pat. No. 6,716,968 and U.S. Pat. No. 6,706,488), mass-spectrometry techniques (which can detect the difference in mass between hypo and hyper acetylated forms of HMGB-1) and HPLC techniques which can determine retention times for these HMGB-1 biomarkers.

In an embodiment of the invention, the hypo and/or hyper-acetylated forms of HMGB-1 are detected by an immunological based assay (e.g. an ELISA).

In an alternative embodiment, the hypo and/or hyper-acetylated forms of HMGB-1 can be detected and quantified using LC-MS/MS. Furthermore, the data can be conveniently generated in a single assay.

The sequences of HMGB-1 in the human, mouse and rat are shown in SEQ ID NOs: 10, 11 and 12 respectively.

For LC-MS/MS detection, the serum HMGB-1 is suitably subjected to partial digestion with an enzyme that cleaves the protein into peptide fragments prior to mass spectrometry detection.

It is the lysine residues present in the HMGB-1 protein sequence that become acetylated in the hyper-acetylated form of HMGB1. Accordingly, mass spectrometry techniques can be used to detect the mass difference between the non-acetylated peptide fragments (that correspond with the hypo-acetylated form of HMGB-1) and acetylated peptide fragments (that correspond with the hyper-acetylated form).

Suitably, the HMGB-1 peptide fragments detected by mass spectrometry comprise at least one lysine residue. Preferably, the peptide fragment detected comprises two or more lysine residues and, even more preferably, three or more lysine residues.

In a particular embodiment, the peptide fragment formed by the partial digestion of HMGB-1 comprises one or more lysine residues from the nuclear localisation region of the HMGB-1 protein. The lysine residues present within this region are lysines 172, 173, 177, 180 and 182-5, as shown in FIG. 10.

In a particular embodiment, the enzyme GLuC is used to partially digest the serum HMGB-1. GLuC generates the fragment shown in SEQ ID Nos. 13, 14 or 15. The difference between the non-acetylated form of the sequence shown in SEQ ID Nos. 13, 14 or 15, and the acetylated form, which carries an additional five acetyl groups on the lysine residues, can be readily detected by mass spectrometry.

The protein HMGB-1 is also known to exist in an oxidised form. The oxidised form of HMGB-1 consists of an oxidised sulfhydryl group of C106 in the cytokine domain of HMGB-1 (see FIG. 7A). The oxidation of the sulfhydryl group of C106 is facilitated by the enzyme caspase and it plays an important role in neutralizing the inflammatory properties of HMGB-1 within apoptotic cells (39). Thus, the presence of the oxidised form of HMGB-1 can also provide an indication of a dampening response counter the inflammatory properties of HMGB-1. Therefore, in an embodiment of the invention, the method of the invention may further comprise the testing of a serum sample to determine the presence of the oxidised form of HMGB-1. The oxidised form of HMGB-1 can be detected by any of the techniques used to detect the hypo and/or hyperacetylated forms of HMGB-1 described herein.

Assay Methodology

In an embodiment of the invention, the specific serum biomarker of apoptosis detected is caspase-cleaved K18.

In an embodiment of the invention, the specific serum biomarkers of necrosis detected are full length K18 and/or the hypo-acetylated form of HMGB-1.

In an embodiment of the invention, the specific serum biomarker of necrosis detected is full length K18.

In an embodiment of the invention, the specific serum biomarker of necrosis detected is the hypo-acetylated form of HMGB-1.

In an embodiment of the invention, the specific serum biomarkers of necrosis detected are full length K18 and the hypo-acetylated form of HMGB-1.

In an embodiment of the invention, the specific biomarker of inflammation detected is the hyper-acetylated form of HMGB-1.

In a further embodiment of the invention, the serum sample is further tested for the presence of the oxidised form of HMGB-1.

Thus, in a particular embodiment, the methodology of the present invention comprises testing a serum sample to determine the presence of:
 (i) caspase-cleaved K18;
 (ii) full length K18 and/or the hypo-acetylated form of HMGB-1; and
 (iii) the hyper-acetylated form of HMGB-1.

In a specific embodiment, the methodology of the present invention comprises testing a serum sample to determine the presence of:
 (i) caspase-cleaved K18;
 (ii) full length K18; and
 (iii) the hyper-acetylated form of HMGB-1.

In another specific embodiment, the methodology of the present invention comprises testing a serum sample to determine the presence of:
 (i) caspase-cleaved K18;
 (ii) the hypo-acetylated form of HMGB-1; and
 (iii) the hyper-acetylated form of HMGB-1.

In a further embodiment, the methodology of the present invention comprises testing a serum sample to determine the presence of:
 (i) caspase-cleaved K18;
 (ii) full length K18 and the hypo-acetylated form of HMGB-1; and
 (iii) the hyper-acetylated form of HMGB-1.

In all of the above-mentioned embodiments, the serum sample may be further tested to detect the presence of the oxidised form of HMGB-1.

As stated above, the K18 and HMGB-1 biomarkers of the present invention can be detected by any suitable means known in the art. For example, both of these biomarkers may be detected by immunologically based assays (such as ELISA and the immunoassays disclosed in U.S. Pat. No. 6,292,850, U.S. Pat. No. 6,716,968 and U.S. Pat. No. 6,706,488), mass-spectrometry techniques and HPLC techniques.

In an embodiment of the invention, the K18 and HMGB-1 biomarkers are detected and quantified using immunological based assays, especially ELISA techniques. ELISA assays are well known and established techniques for detecting protein biomarkers.

In an alternative embodiment, both the K18 and HMGB-1 biomarkers of the present invention can be detected by mass spectrometry, especially LC-MS/MS analysis.

LC-MS/MS detection provides a sensitive and convenient means by which all of the above serum biomarkers (i.e. the marker of apoptosis (caspase-cleaved K18), the markers of necrosis (full length K18 and hypo-acetylated HMGB-1) and the marker of inflammation (hyper-acetylated HMGB-1)) can be detected in a single serum sample. LC-MS/MS also enables the ratio of the two forms of K18 and the two forms HMGB-1 to be determined in parallel. This provides an indication of the relative amounts of apoptosis, necrosis and inflammation occurring.

In an embodiment of the invention, mass spectrometry is used to test the serum sample for the presence of caspase-cleaved K18 (as the specific serum biomarker of apoptosis), full length K18 and the hypo-acetylated form of HMGB-1 (as specific serum biomarkers of necrosis) and the hyper-acetylated form of HMGB-1 (as the specific serum biomarker of inflammation). In order to correlate the presence of apoptosis, necrosis, and/or inflammation with a specific organ or tissue, the presence of one or more of these biomarkers can then be correlated with the presence of an organ or tissue specific indicator of damage, as defined further below.

In an embodiment of the invention, the serum sample obtained from the host is split into two separate samples, one of which is used to detect HMGB-1 and the other of which is used to detect K18. The HMGB-1 sample is then treated with a protease enzyme, such as GLuC, to partially digest the HMGB-1 and form fragments, the hypo- and hyper-acetylated forms of which can then be detected and differentiated by mass spectrometry, as discussed above. The K18 sample is also treated with a protease, such as trypsin, to partially digest the serum K18 proteins into fragments that enable the caspase-cleaved and full length forms to be detected and differentiated by mass spectrometry, as discussed above.

In an alternative embodiment, the method comprises:
separating the K18 and HMGB-1 protein components from the serum sample; and
partially digesting the K18 protein to form fragments that can be detected by mass spectrometry; and
partially digesting the HMGB-1 protein to form fragments that can be detected by mass spectrometry.

The K18 and HMGB-1 proteins can be separated from other serum components and isolated using any suitable protein separation technique, for example, immunoprecipitation, SDS-PAGE gel electrophoresis, Western Blotting or chromatography. Suitably SDS-PAGE or Western Blotting is used to separate the serum proteins. Appropriate standards can be used to identify the K18 and HMGB-1 generated by the protein separation techniques.

Any suitable enzyme may be used to partially digest the proteins as discussed above.

Following partial digestion, the fragments of K18 and HMGB-1 can then be detected by mass spectrometry.

In an embodiment, the methodology of the present invention suitably further comprises assaying for a specific indicator of organ or tissue damage. In many cases, this will involve assaying for an organ or tissue specific biomarker of damage, as discussed further below.

Organ or Tissue Specific Indicators of Damage

The reference to an "organ or tissue specific indicator of damage" is used herein to refer to a clinical indicator of injury or damage which is associated with a particular organ or tissue.

In the case of the liver, for example, the "organ specific indicator of damage" may be another biomarker which is associated with hepatotoxicity or another accepted clinical measure of liver function. In an embodiment of the invention, the liver specific indicator of damage is a serum biomarker, the presence of which is associated with liver injury. The detection of a liver-specific biomarker of injury, together with one or more of the specific serum biomarkers of apoptosis, necrosis, and/or inflammation enables any apoptosis, necrosis or inflammation detected to be correlated with injury occurring in the liver. Particular examples of liver-specific biomarkers associated with liver injury include ALT (alanine aminotransaminase), AST (aspartate aminotransaminase), AP (alkaline phosphatase), GLDH (glutamate dehydrogenase), and GGT (gamma-glutamyl transpeptidase). Methods of analysing for the presence of these biomarkers are well known and any suitable method may be used in accordance with the methods of the present invention.

In the case of skin tissue, the "tissue specific indicator of damage" may be the presence of a clinical skin condition (such as a rash, swelling, itching etc). The presence of a skin condition, together with one or more of the specific serum biomarkers of apoptosis, necrosis, and/or inflammation enables any apoptosis, necrosis or inflammation detected to be correlated with injury occurring in the skin tissue.

In the case of the lung, the "organ-specific indicators of damage" may include one or more of surfactant protein-D, surfactant protein-A, or syndecan 1. Methods of analysing for the presence of these biomarkers are known in the art and any suitable method may be used in accordance with the methods of the present invention.

In the case of the kidneys, the "organ-specific indicators of damage" may include one or more of KIM-1, clusterin, osteopontin, β2-microglobulin, retinol binding protein, R-NAG (N-acetyl-B-D-glucosamidase), Cystatin-C, albumin, GSTα, lipocalin (NGAL) or IL-18. Methods of analysing for the presence of these biomarkers are known in the art and any suitable method may be used in accordance with the methods of the present invention.

In the case of the cardiovascular system, the indicator of damage may be cardiac troponin T and/or I (cTnT, cTnI). Methods of analysing for the presence of these biomarkers are known in the art and any suitable method may be used in accordance with the methods of the present invention.

In a particular embodiment, the methodology of the present invention additionally comprises assaying for the presence of a plurality of specific indicators of organ or tissue damage associated with different organs or tissues so that and apoptosis, necrosis or inflammation detected can be correlated with damage occurring in one or more specific organs or tissues.

Applications

The methodology of present invention is particularly useful for monitoring the occurrence of apoptosis, necrosis and/or inflammation in a human or animal subject following the administration of a chemical agent, such as, for example, a new drug.

Thus, the present invention provides, in one aspect, a method of monitoring the pathogenesis of organ or tissue damage caused by the administration of a drug to a human or animal subject, said method comprising testing a serum sample from said subject to determine the presence of:

(i) a specific serum biomarker of apoptosis as defined herein;
(ii) a specific serum biomarker of necrosis as defined herein; and
(iii) a specific serum biomarker of inflammation as defined herein; and
correlating the presence of one or more of said serum biomarkers with an organ or tissue specific indicator of damage.

Suitably, the method further comprises correlating the level of the serum biomarkers with predetermined levels to provide an indication of the severity of the drug-induced organ or tissue damage.

Suitably, the method comprises comparing the levels of the serum biomarkers detected with predetermined levels. The predetermined level may be a baseline level obtained from the subject prior to the commencement of the administration of the drug.

Typically the higher the level of the biomarkers detected, the greater the severity of the organ or tissue injury that is occurring.

The methodology can also be used to monitor the progression of apoptosis, necrosis, and/or inflammation over time by testing serum samples acquired from the subject over a selected period of time. The ability to quickly assess the presence of the biomarkers concerned enables the rapid feedback of information to scientists and/or clinicians.

The methods of the present invention are particularly useful for the detection, assessment and diagnosis of liver, skin, kidney, lung or cardiovascular injury/toxicity or a combination thereof.

(i) Assessing Liver Damage

In a particular embodiment, the present invention provides a method of detecting and/or assessing the presence of drug induced liver damage, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a liver specific indicator of damage as defined herein.

In a further embodiment, the present invention provides a method of diagnosing drug induced liver damage which comprises testing a serum sample obtained from an animal or human to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with liver specific indicator of damage as defined herein.

In a further embodiment, the present invention provides a method of detecting and/or assessing the presence of drug induced apoptosis, necrosis and inflammation in the liver, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a liver specific indicator of damage as defined herein.

Suitably, any method known in the art for detecting the liver specific indicator of damage is utilised. For example, if ALT is detected as the liver specific indicator of damage, it can be measured using the techniques described in Cummings et al. (17).

(ii) Assessing Skin Damage

In a particular embodiment, the present invention provides a method of detecting and/or assessing the presence of drug induced skin damage, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a clinical indicator of skin damage as defined herein.

In a further embodiment, the present invention provides a method of detecting and/or assessing the presence of drug induced apoptosis, necrosis and inflammation in skin, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a clinical indicator of skin damage as defined herein.

Suitably, the method of detecting, assessing and/or diagnosing liver or liver damage defined above involves the detection of caspase-cleaved K18 as the specific serum biomarker of apoptosis, full length K18 and the hypo-acetylated form of HMGB-1 as the specific serum biomarker of necrosis and the hyper-acetylated form of HMGB-1 as the specific serum biomarker of inflammation. All of which can be conveniently detected by LC-MS/MS.

The clinical indicator of skin damage is suitably the presence of a clinical skin condition (such as a rash, swelling, itching etc).

(iii) Assessing Lung Damage

In a particular embodiment, the present invention provides a method of detecting and/or assessing the presence of drug induced lung damage, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a lung specific indicator of damage as defined herein.

In a further embodiment, the present invention provides a method of diagnosing drug induced lung damage which comprises testing a serum sample obtained from an animal or human to determine the presence of:

(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with lung specific indicator of damage as defined herein.

In a further embodiment, the present invention provides a method of detecting and/or assessing the presence of drug induced apoptosis, necrosis and inflammation in the lung, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a lung specific indicator of damage as defined herein.

Suitably, any method known in the art for detecting the lung specific indicator of damage is utilised.

(iv) Assessing Kidney Damage

In a particular embodiment, the present invention provides a method of detecting and/or assessing the presence of drug induced kidney damage, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a kidney specific indicator of damage as defined herein.

In a further embodiment, the present invention provides a method of diagnosing drug induced lung damage which comprises testing a serum sample obtained from an animal or human to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with kidney specific indicator of damage as defined herein.

In a further embodiment, the present invention provides a method of detecting and/or assessing the presence of drug induced apoptosis, necrosis and inflammation in the kidney, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a kidney specific indicator of damage as defined herein.

Suitably, any method known in the art for detecting the kidney specific indicator of damage is utilised.

(v) Assessing Cardiovascular Damage

In a particular embodiment, the present invention provides a method of detecting and/or assessing the presence of drug induced cardiovascular damage, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a cardiac specific indicator of damage as defined herein.

In a further embodiment, the present invention provides a method of diagnosing drug induced cardiovascular damage which comprises testing a serum sample obtained from an animal or human to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with cardiovascular specific indicator of damage as defined herein.

In a further embodiment, the present invention provides a method of detecting and/or assessing the presence of drug induced apoptosis, necrosis and inflammation in the cardiovascular tissue, which comprises testing a serum sample to determine the presence of:
(i) a specific serum biomarker of apoptosis as defined herein;
(ii) a specific serum biomarker of necrosis as defined herein;
(iii) a specific serum biomarker of inflammation as defined herein; and
correlating the presence of one or more of said serum biomarkers with a cardiovascular specific indicator of damage as defined herein.

Suitably, any method known in the art for detecting the lung specific indicator of damage is utilised.

The present invention also provides the use of the biomarkers defined herein in the detection and/or assessment of organ or tissue injury.

Assays/Kits

The present invention also provides an assay for detecting and/or assessing drug-induced organ or tissue damage, said assay comprising:
means for detecting a specific serum biomarker of apoptosis as defined herein;
means for detecting a specific serum biomarker of necrosis as defined herein; and
means for detecting a specific serum biomarker of inflammation as defined herein.

Suitably, the assay further comprises means for detecting one or more organ or tissue specific injury biomarkers to enable any apoptosis, necrosis or inflammation detected to be correlated with one or more particular organs and/or tissues.

In an embodiment, the assay further comprises means for detecting the oxidized form of HMGB-1.

Suitably, the means for detecting a specific serum biomarker of apoptosis, necrosis and/or inflammation is selected from mass spectrometry or an immunological assay, such as an ELISA.

In an embodiment, the means for detecting one or more organ or tissue specific injury biomarkers is an immunological assay, such as ELISA.

The present invention also provides a kit for detecting and/or assessing drug induced organ or tissue injury, said kit comprising:

reagents for detecting caspase cleaved K18;

reagents for detecting full length K18 and/or the hypoacetylated form of HMGB-1;

reagents for detecting the hyper acetylated form of HMGB-1.

In an embodiment, the kit further comprises reagents for detecting the presence of the oxidized form of HMGB-1.

In an embodiment, the reagents are reagents necessary to enable the biomarkers to be detected by ELISA. Such reagents may include antibodies specific for caspase-cleaved K18, full length K18 and/or the hypoacetylated form of HMGB-1 and the hyperacetylated form of HMGB-1.

In alternative embodiment, the kit may be a kit for detecting the biomarkers by mass spectrometry. Such a kit may comprise:

an enzyme for the partial digestion of serum K18 as defined hereinbefore;

an enzyme for the partial digestion of serum HMGB-1 as defined hereinbefore; and instructions detailing how to test the sample in accordance with any one of the methods defined herein to determine whether apoptosis, necrosis and/or inflammation is occurring.

The kits of the present invention may further comprise reagents for detecting the presence of an organ specific indicator of organ damage. Such reagents could include, by way of example, any reagents that are required to detect any of the liver, kidney, lung and/or cardiac injury biomarkers defined herein. For example, if the kit is to be used for detecting liver damage, the liver-specific biomarker could be ALT, in which case the kit may further comprise ThermoTrace Infinity ALT Liquid stable reagent, which is used in accordance with the manufacturer's instructions.

In an embodiment, the kit further comprises reagents for enabling the separation of serum proteins. Such reagents may include reagents for SDS-PAGE electrophoresis or Western blotting. Such reagents may include any standards run on the gels to enable the identification of the K18 and HMGB-1 bands and/or any reagents needed to form the gels themselves. Alternatively, the kit may comprise a separation column.

Suitably, the kit further comprises a substrate for holding a serum sample.

The kit of the present invention may be used in conjunction with standard laboratory equipment in order to facilitate the detection and assessment of apoptosis, necrosis and/or inflammation by assessing the presence of the K-18 and HMGB-1 biomarkers in a sample. A mass spectrometer is an essential additional piece of equipment for the detection of the fragments of K18 and HMGB-1 formed by the partial enzymatic digestion.

BRIEF DESCRIPTION OF THE DRAWINGS AND TABLES

The invention is described further below in reference to the following figures, in which:

FIG. 1 shows SDS-PAGE and coomassie analysis of (A) HMGB1 and K18 forms isolated by IP from the sera of mice administered APAP (530 mg/kg; 5 hr) or 0.9% saline. (B) MS/MS analysis of murine HMGB1 acetylated on lysine residues 180, 182-185 and (C) schematic overview of lysines within murine HMGB1 with identified acetylated residues by MS/MS within the nuclear localisation sequence present in the sera of APAP dosed mice. (D) MS/MS characterization of 47 kDa full length K18 with an intact caspase cleavage motif and (E) fragmented K18 with the caspase cleavage motif cut present only in the 44 and 21 kDa variants. Figures are representative of 6 animals per group.

Figure 2:
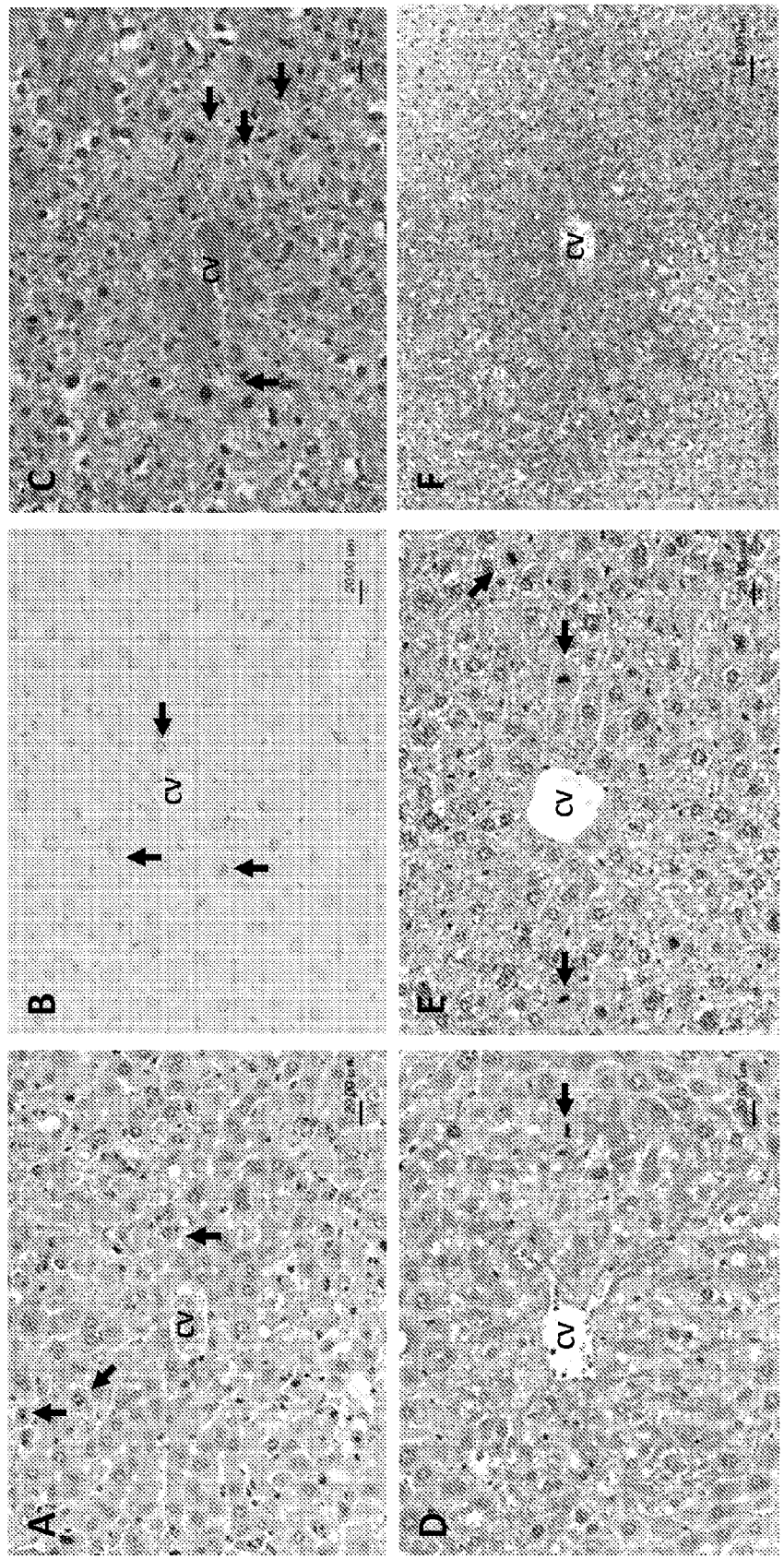

FIG. 2 shows murine (A) H&E stained liver sections and (B) immunohistological demonstration of hepatic cleaved caspase-3 at 3 hr post APAP dose (530 mg/kg). Arrows indicate hepatocytes showing apoptotic morphology and active caspase-3 positive cells. (C) H&E stained murine liver section 5 hr post APAP dose (530 mg/kg) with black arrows indicating necrotic hepatocytes. H&E stained murine liver sections (D) 15 hr and (E) 24 hr post APAP dose (530 mg/kg) with hepatocytes exhibiting mitotic morphology indicated by a black arrow. All sections 20×. magnification. (F) H&E stained murine liver sections 5 hr following APAP+Z-VAD.fmk treatment (10×. magnification). CV, central vein. Figures are representative of 6 animals per group.

Figure 3:
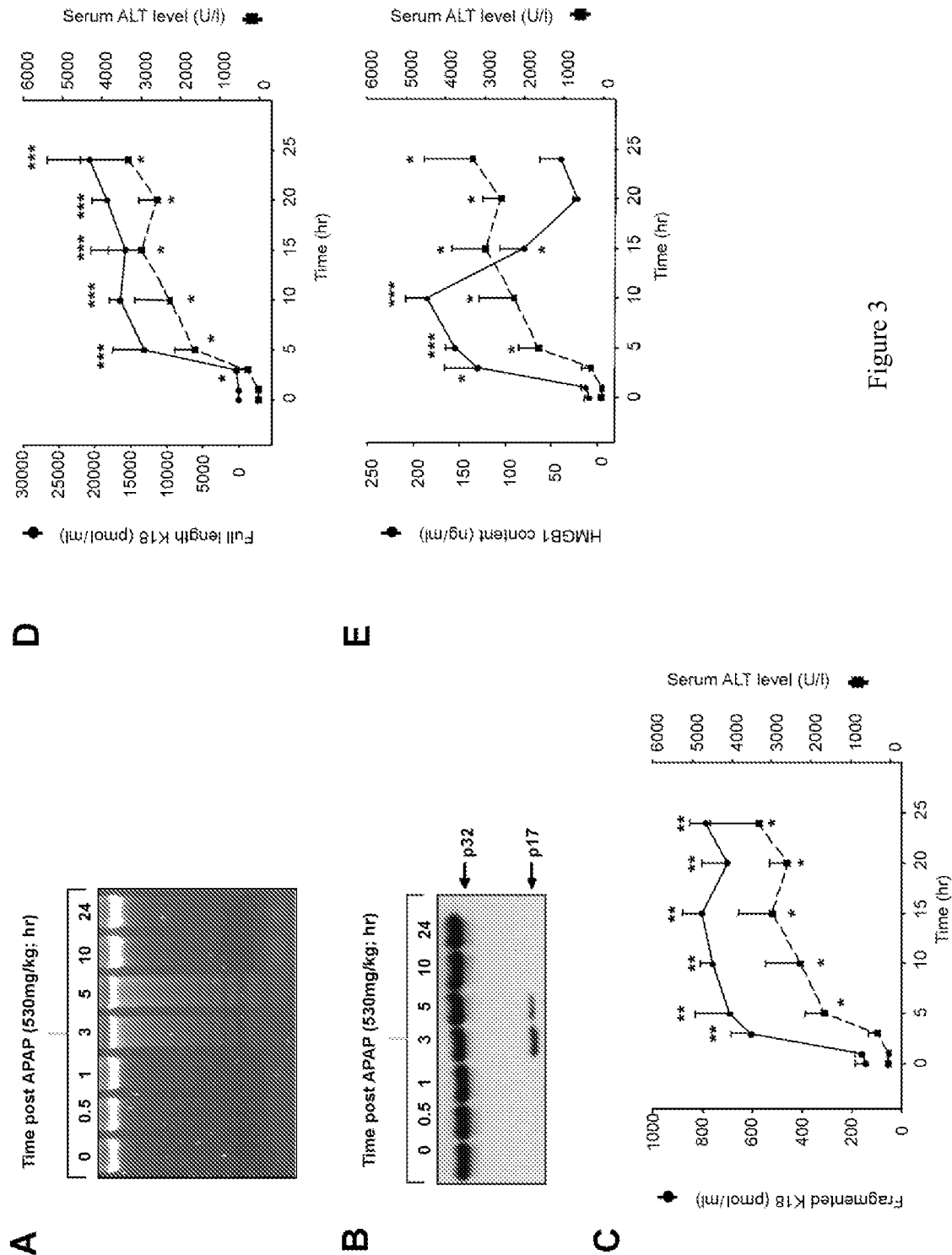

FIG. 3 shows time course evaluation following APAP administration (530 mg/kg; 0-24 hr) of (A) hepatic DNA laddering determined by agarose gel analysis, (B) processing of hepatic pro-caspase-3 (p32) to the active fragment (p17) determined by western blot. Simultaneous time course correlation of ALT activity (dotted line; U/I) with (C) caspase cleaved K18 fragment level (solid line; pmol/ml), (D) full length K18 level (solid line; pmol/ml) and (E) total HMGB1 level (solid line; ng/ml) present in the serum of APAP dosed mice (530 mg/kg). Figures are representative of 6 animals per group. Data given as mean±S.D. Statistical significance was assigned relative to vehicle treated controls from the same time point as defined in materials and methods. *$p<0.05$, $p<0.01$ and *$p<0.005$.

Figure 4:
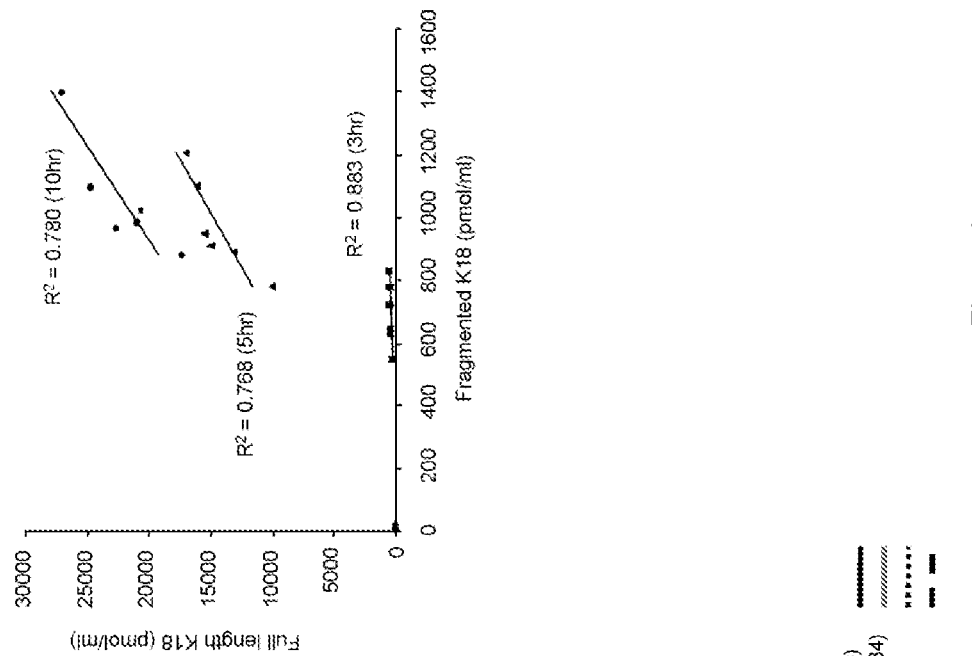
Figure 4:
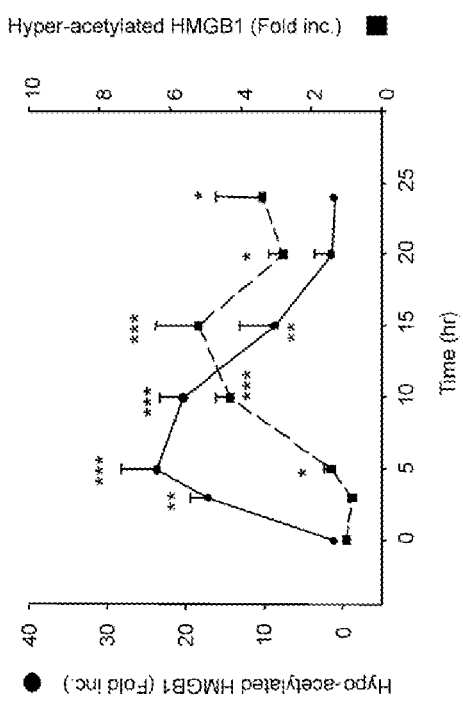
Figure 4:
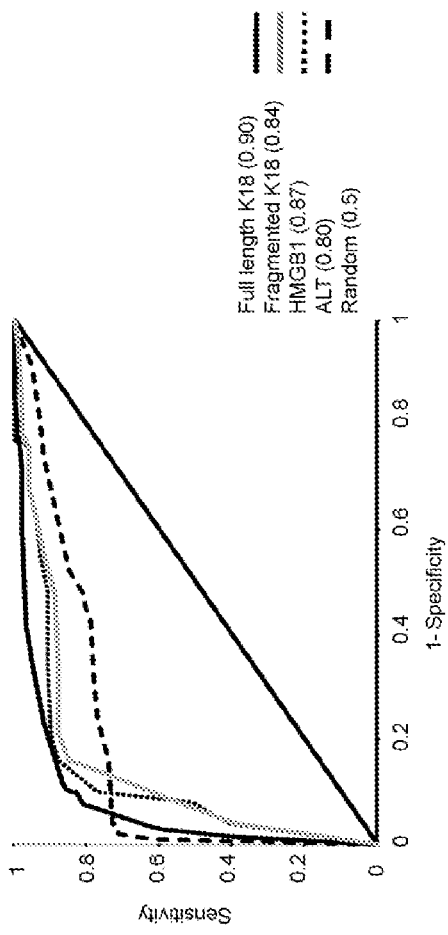

FIG. 4 shows (A) Fold increase in serum hyper (immune cell derived—dotted line) and hypo (released by necrotic cells—solid line) acetylated HMGB1 over 0-24 hr and (B) correlation of serum caspase cleaved K18 as a marker of apoptosis against full length K18 as a marker of necrosis in individual mice over 10 hr following APAP administration (530 mg/kg), correlation coefficients given when required. (C)ROC analysis indicating sensitivity and 1-specificity of serum K18, fragmented K18, HMGB1 and ALT as biomarkers of APAP hepatotoxicity in the mouse. Data is given as mean±S.D of 6 mice per group. Statistical significance was assigned relative to time matched vehicle dosed controls. *$p<0.05$, $p<0.01$ and *$p<0.005$.

Figure 5:
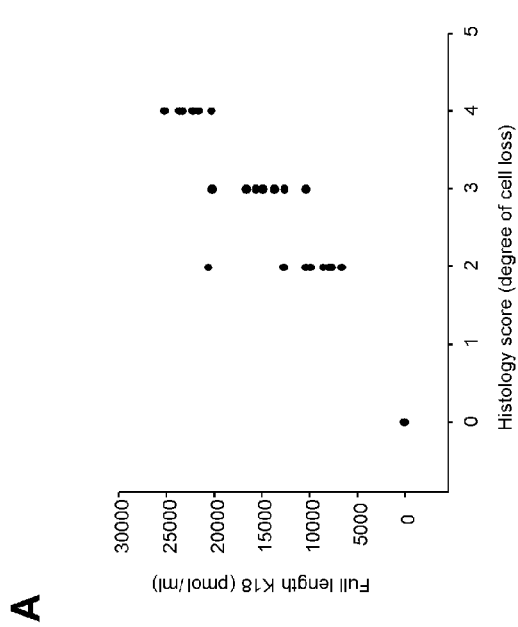

FIG. 5 shows correlation of individual animal serum (A) full length K18 level (pmol/ml) and (B) total HMGB1 content (ng/ml) with the degree of cell loss (histology score). Correlation of individual animal serum ALT activity (U/I) with (C) full length K18 level and (D) total HMGB1 content following APAP administration (530 mg/kg; 5 hr). Correlation coefficients indicated were required.

Figure 6:
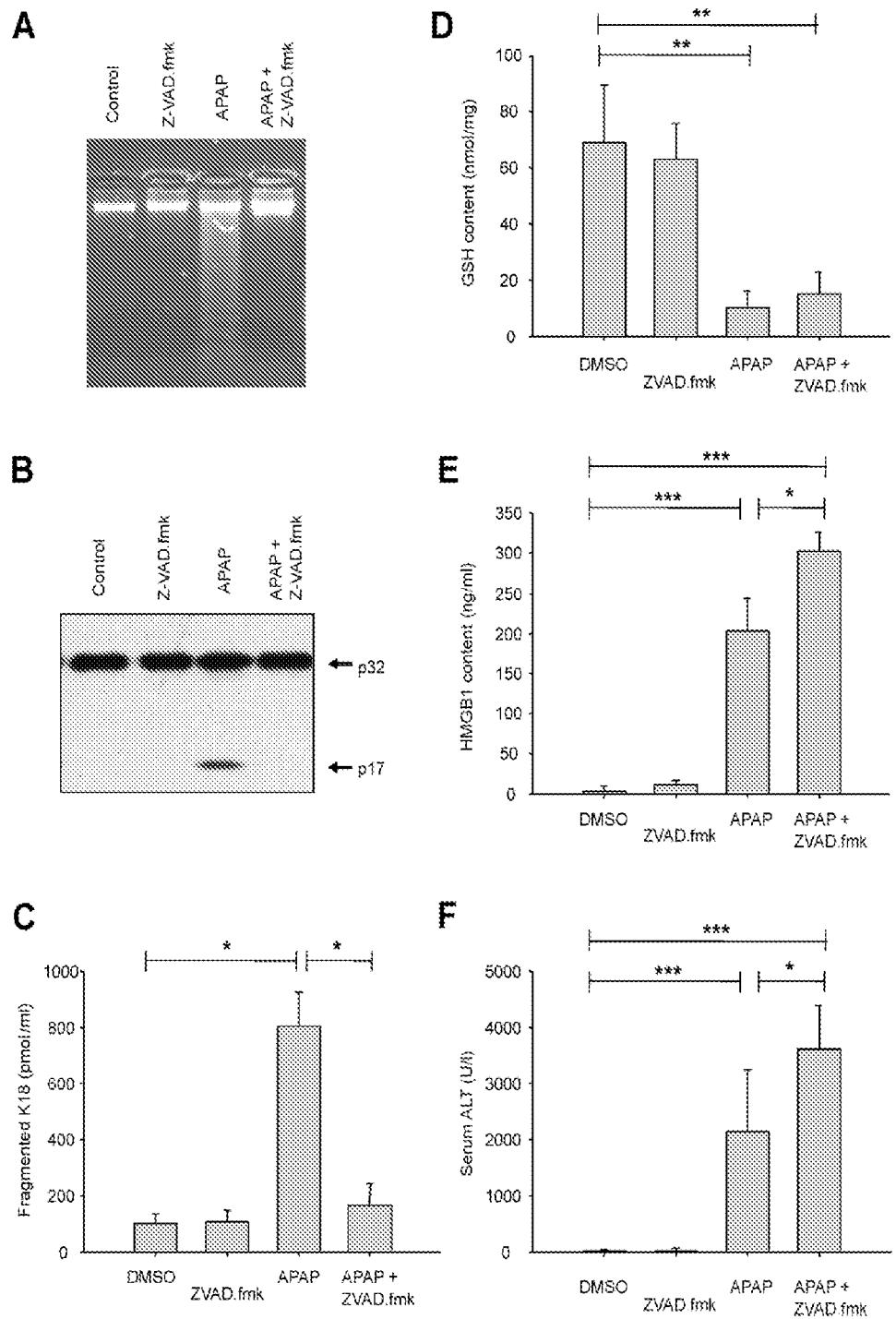

FIG. 6 shows the effect of Z-VAD.fmk on APAP-induced (530 mg/kg; 5 hr) (A) hepatic DNA laddering, (B) pro-caspase 3 processing, (C) serum caspase cleaved K18 abundance (pmol/ml), (D) hepatic GSH depletion (nmol/mg), (E) total serum HMGB1 content (ng/ml) and (F) serum ALT activity (U/l) recorded simultaneously within the same group of mice. Data is representative of mean±S.D of 6 mice per group. Statistical significance was assigned relative to time matched vehicle dosed controls. *p<0.05, p<0.01 and *p<0.005.

Figure 7:
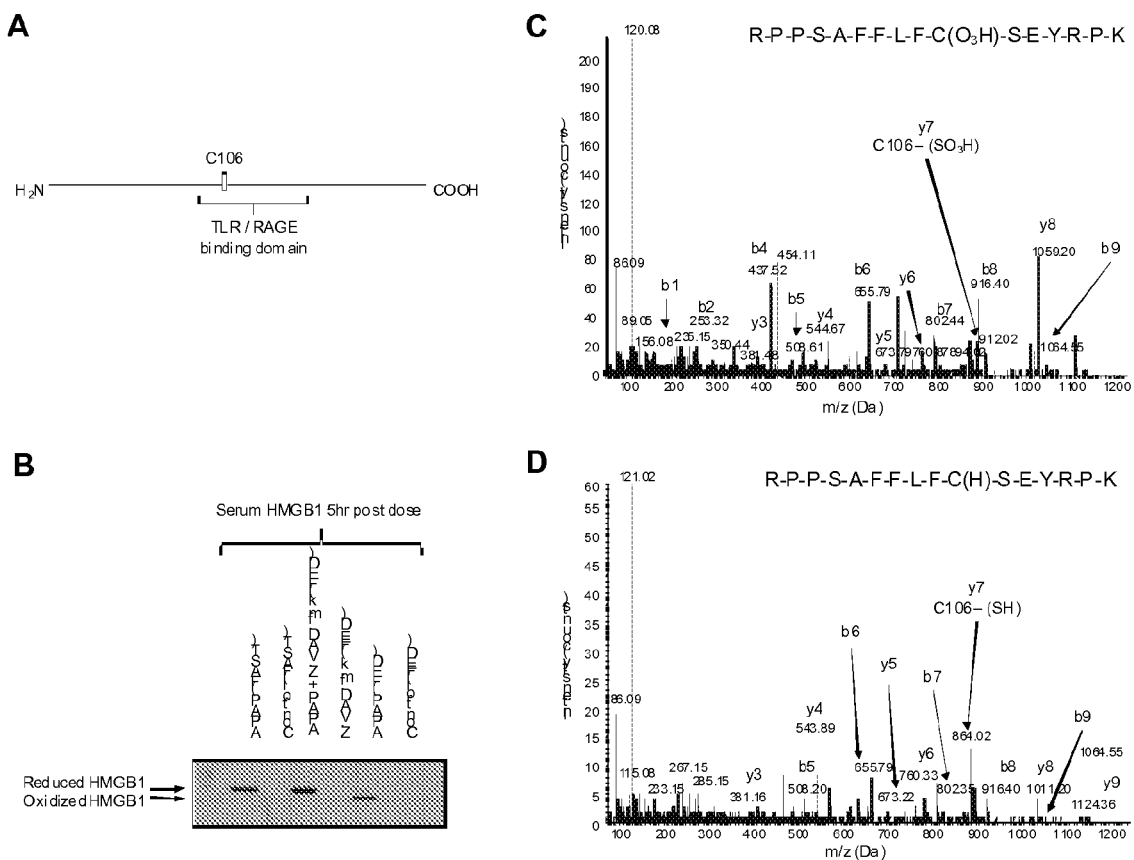

FIG. 7 shows the characterization of the cysteine 106 HMGB-1 oxidation status with the sera of acetaminophen (APAP) (530 mg/kg; 5 h) dose mice. (A) Schematic overview of the location of cysteine 106 within the cytokine domain of murine HMGB-1 which is characterized by MS/MS. (B) Non-reducing SDS-PAGE separation and western analysis of reduced and oxidized HMGB-1 isolated by immunoprecipitation from the sera of fed and fasted APAP dosed mice (530 mg/kg; 5 h). HMGB-1 was also isolated from Z-VAD.fmk pre-treated APAP dosed mice. (C) MS/MS analysis of oxidized murine HMGB-1 peptide 97-112 from a fed APAP treated mouse containing the cysteine 106 sulfonic acid. (D) MS/MS analysis of reduced murine HMGB-1 peptide 97-112 containing the cysteine 106 thiol from an APAP treated mouse which was pre-fasted for 24 h. MS/MS and western figures are representative of 6 mice per group.

Table 1 shows a summary of histological changes, induction of apoptotic biomarkers (caspase-3 activation and DNA laddering) and serum biomarker evaluation induced by APAP in male CD-1 mice (530 mg/kg) over 3-24 hr. For Immunohistology (1H), + indicates the degree of hepatic cleaved caspase-3. For GSH depletion, (+) indicates significant or (−) non-significant hepatic GSH depletion compared to control animals. (+) indicates positive detection of DNA laddering or processing of caspase-3 by western blot (WB). For serum biomarker analysis, (+) indicates a significant elevation above control values or (−) no significant increase above control values.

EXAMPLES

The invention will now be described in more detail in relation to the following illustrative examples.

Example 1

Bioanalysis of Keratin-18 and High Mobility Group Box Protein-1 as Biomarkers of Acetaminophen-Induced Apoptosis and Necrosis Acetaminophen (APAP), a model hepatotoxin in rodent systems and a significant clinical ADR, can be used to investigate potential informative and mechanism based biomarkers of DILI. The biochemical events leading to the initiation of APAP hepatotoxicity through the cytochrome P450 mediated formation of the reactive metabolite, N-acetyl-p-benzoquinoneimine (NAPQI), and subsequent requirement for GSH depletion, are well defined (5). Although necrosis is the final and ultimate form of cell death, several reports suggest that intra-cellular events following APAP metabolic activation can lead to hepatocyte apoptosis (6-8). However, the extent to which APAP induces apoptosis remains controversial (9-11).

The aim of this investigation was to define the dynamics between apoptosis and necrosis within an animal model of APAP-induced hepatotoxicity through the non-invasive analysis of HMGB1 and K18 as serum biomarkers of cell death. LC-MS/MS methods were utilized to characterize and quantify differing molecular forms of serum HMGB1 released by innate immune or necrotic cells. In parallel, LC-MS/MS was also utilized to confirm caspase cleavage of K18 following APAP-induced apoptosis and to quantify serum fragments and full length K18 in the mouse.

Material and Methods

Materials

Antibodies to HMGB1 and K18 (rabbit anti-human) were purchased from Abcam (Cambridge, U.K), antibodies to caspase 3 for both western (rabbit anti-caspase-3, 8G10) and immunohistological (rabbit anti-cleaved caspase, 5A1E) analysis were purchased from Cell signalling (Hitchin, U.K). Secondary antibodies for immunohistology were obtained from HMGB1 ELISA kit was purchased from Shino-Test Corporation (Tokyo, Japan), Infinity ALT liquid reagent was purchased from Alpha Laboratories (Eastleigh, U.K.). Bio-Rad Protein Assay Dye Reagent was purchased from Bio-Rad Laboratories Ltd (Hemel Hempstead, U.K.). For proteomic analysis α-cyano-4-hydroxycinnamic acid was purchased from LaserBiolabs (France), Trypsin from promega (U.K) and ZipTips from Millipore (U.K). All solvents were of HPLC grade and were the products of Fischer Scientific plc (Loughborough, U.K.). Unless otherwise stated, all other chemicals, peptide standards and materials were purchased from Sigma-Aldrich (Poole, U.K).

Animal Treatment

Groups of 6 individual male CD-1 mice (25-35 g) with free access to food and water were included into the study. For a time course study animals were administered a single i.p injection of APAP (530 mg/kg) in 0.9% saline and were euthanized 3, 5, 10, 15, 20 or 24 hr after treatment. Control animals received either 0.9% saline or solvent control in 0.9% saline as appropriate. As a negative control for apoptosis and to validate apoptotic serum biomarkers, one group of mice received the pan-caspase inhibitor Z-VAD.fmk (10 mg/kg i.v in DMSO (0.1 ml/kg DMSO in 0.9% saline 15 min pre-APAP dose) and was euthanized 5 hr after treatment. Serum ALT activity, HMGB1 and K18 were determined as well as DNA laddering, caspase-3 western blotting, GSH content and histology including immunohistology was performed on all animals.

Hepatotoxicity Assessment

Animals were euthanized by $CO_2$ inhalation and cervical dislocation, blood was collected by cardiac puncture. Blood samples were stored at 4° C. and allowed to clot overnight. Livers were removed, rinsed in ice cold saline, and fixed in 10% neutral buffered formalin or snap frozen. Serum alanine transaminase (ALT) levels were determined as previously reported (28). For histological assessment of hepatotoxicity and immunohistological examination, formalin-fixed liver sections were routinely paraffin wax embedded. 3-5 µm sections were prepared and stained with haematoxylin and eosin (H&E) or used for immunohistology. H&E stained sections were examined for any histopathological features and the identification of apoptotic and/or necrotic hepatocytes. The degree of (predominantly centrilobular) hepatocyte loss was scored 0-5, where 0 indicated no evidence of cell loss (unaltered liver) and 5 extensive cell losses. The latter was performed blind and independently by two co-authors (DJA, AK).

Determination of Hepatic Glutathione Levels

Total hepatic glutathione (GSH+GSSG) levels were determined as described previously (29).

Caspase-3 Western Blotting, Immunohistological Demonstration of Cleaved Caspase-3 and DNA Laddering Caspase-3 western blotting was carried out as described previously (30) on mouse liver cytosol fractions prepared from snap frozen livers. DNA was isolated from snap frozen livers using the Sigma-Aldrich GeneElute kit according to the manufacturer's instructions. DNA laddering was visualised through ethidium bromide staining following separation on a 1% agarose gel. For the immunohistological demonstration of cleaved caspase-3 the peroxidase anti-peroxidase method was applied on formalin-fixed, paraffin-embedded liver sections, based on previously described protocols (31). The number of cleaved caspase-3 positive cells (cytoplasmic staining) was evaluated semi-quantitatively (− no positive cells; + scattered positive cells; ++ moderate number of positive cells, +++ numerous positive cells).

Serum HMGB1 and K18 Characterization and Quantification

Overnight immunoprecipitations (IP) of serum K18 and HMGB1 (5 µg antibody and protein G separation) were subjected to SDS-PAGE. Protein bands were excised from Coomassie Blue-stained gels, destained by incubation with 50% acetonitrile/50 mM ammonium bicarbonate followed by vacuum drying. Gel pieces were rehydrated in 50 mM ammonium bicarbonate containing 40 ng/µL modified trypsin (K18) or GluC (HMGB1) and incubated for 16 hr at 37° C. Peptides were extracted by incubation with 2 changes of 60% acetonitrile/1% trifluoroacetic acid and the resulting supernatants were again dried. Extracts were desalted using C18 ZipTips according to the manufacturer's instructions and reconstituted in 5% acetonitrile/0.1% trifluoroacetic acid. For LC-MS/MS analysis, samples were delivered into a QSTAR Pulsar i hybrid mass spectrometer (Applied Biosystems) by automated in-line liquid chromatography (integrated LC-Packings System, 5 mm C18 nano-precolumn and 75 µm×15 cm C18 PepMap column (Dionex, Calif., USA) via a nano-electrospray source head and 10 µm inner diameter PicoTip (New Objective, USA). A gradient from 5% acetonitrile/0.05% trifluoroacetic acid (v/v) to 48% acetonitrile/0.05% trifluoroacetic acid (v/v) in 60 min was applied at a flow rate of 300 mL/min, MS and MS/MS spectra were acquired automatically in positive ion mode using information-dependent acquisition (Analyst, Applied Biosystems). Database searching was performed using Protein Pilot 2 (Applied Biosystems) with the latest version of the SwissProt database, with the confidence level set at 80%, and with biological modifications allowed. Quantification of murine serum full length K18 and caspase dependent K18 fragments was accomplished through construction of standard curves generated with synthetic peptide standards spiked into and could be recovered from control serum and compared to immunoassay (17). The full length K18 standard (LLEDGEDFSLNDALDSSNSMQTVQK) was designed to span the caspase 3, 7, 9 cleavage site, whereas the abbreviated peptide (LLEDGEDFSLNDALD) is only derived from K18 fragments with the caspase cleavage site cut (limit of detection; 300 fmol/ml. coefficient of variation; <10%). HMGB1 and its hyper-acetylated derivative were quantified by spectral counting of the peptide peak, since no synthetic standards were available, and are consequently presented only as relative values and compared to total levels determined by ELISA according to the manufacturer's instructions (limit of detection; 0.1 ng/ml. coefficient of variation; <10%).

Statistical Analysis

All results (excluding histological analysis) are expressed as mean±standard deviation (S.D). Values to be compared were analysed for non-normality using a Shapiro-Wilk test. The unpaired t-test was used when normality was indicated. A Mann-Whitney U test was used for non-parametric data. All calculations were performed using StatsDirect statistical software, results were considered to be significant when p<0.05.

Results

Identification and Characterization of Circulating Molecular Forms of HMGB1 and K18 During APAP-Induced Hepatotoxicity LC-MS/MS characterized of HMGB1 present in the sera of APAP dosed mice, but not control (FIG. 1A) revealed a mixture of both hypo-acetylated (released with necrosis) or hyper-acetylated (released from activated immune cells) HMGB1. GluC digested HMGB1 and MS/MS analysis identified a peptide of 1132.6 Da containing lysine residues 180-185 present within the HMGB1 nuclear localization sequence. A peptide was also present containing the same amino acid sequence but had a mass increase of 210 amu. The increase in mass to 1342.6 Da corresponded to the addition of 5 acetyl groups. Further MS/MS analysis confirmed the acetylation modifications to be present on lysine residues 180-185 (FIG. 1B-C), a key mechanism for its active release by monocytes and macrophages. A schematic HMGB1 lysine map is shown in FIG. 1C with acetylated residues characterized in the sera of APAP dosed mice.

Characterization of K18 present in the sera of APAP dosed mice resulted in the identification of the full length K18 (47 kDa) released from necrotic cells and 2 apoptosis related forms at 44 and 21 kDa (FIG. 1A). In contrast, in the sera of untreated mice, no evidence was found for the release of the full length or fragmented forms of K18 (FIG. 1A). MS/MS analysis of the full length K18 yielded a 2756 Da peptide that is not present in the caspase dependent apoptosis fragments of K18 (44 and 21 kDa). Analysis characterized this peptide as having the predicted caspase 3, 7 and 9 cleavage motif intact (FIG. 1D). In contrast, tryptic digestion of the 44 and 21 kDa K18 fragments yielded a foreshortened peptide of 1665 Da absent from the full length K18. MS analysis revealed that this was due to the presence of the caspase site being cleaved at the DALD/SS motif (FIG. 1E).

K18 and HMGB1 Represent Sensitive and Informative Mechanism-Based Biomarkers of APAP Induced Histological Changes Control animals did not show any histological changes, i.e. there was no evidence of hepatocyte loss (score 0), necrosis or apoptosis by histology including immunohistology for cleaved caspase-3. At 3 hr post treatment, centrilobular cell loss (score 1-2) was observed and there were numerous cells with the morphology of apoptotic cells, mainly centrilobular (FIG. 2A). Apoptosis was confirmed by the expression of cleaved caspase-3 (FIG. 2B) and by DNA laddering and caspase-3 processing as well as serum K18 fragment elevation (FIG. 3). At 5 hr post treatment, animals exhibit a variable degree of cell loss (score 1-3, average 2). Apoptotic cells decreased in number but were generally numerous with a score of 1 and necrotic cells increased (FIG. 2.C). When apoptotic cells were not identified in situ, DNA laddering and/or caspase 3 processing and an elevation of serum K18 fragments was generally not observed either. By 10 hr post treatment, cell loss was scored 1 or 2 and apoptotic cells were rare, if observed at all. There was no evidence of DNA laddering or caspase 3 processing and serum K18 fragment elevation was still observed. At 15 hr post treatment, serum K18 fragments were still elevated. Hepatocyte loss was scored 0-2 (average 1 or 2) and there was evidence of hepatocyte replacement in zone 3 (centrilobular) (FIG. 2D). At 20 hr post treatment, there was no distinct evidence of or only minimal hepatocyte loss (score 0 or 1), but hepatocytes in zone 3 appeared irregularly arranged. The latter was not observed any more at 24 hr post treatment, when all livers were scored 0. From 5 hr post treatment, there was evidence of increased hepatocyte mitosis, represented by mitotic figures. These were particularly numerous at 15, 20 and 24 hr post treatment (FIG. 2D-E). Serum full length K18 elevation and increased serum ALT activity was observed over the entire time course (FIG. 3D), while serum HMGB1 elevation was not seen beyond 15 hr post treatment (FIG. 3E) and GSH depletion was only obvious 3 and 5 hr post treatment. At no time point after treatment significant inflammatory cell infiltration was observed, although between 5 and 15 hr small numbers of neutrophils were seen centrilobularly in some animals. Results are summarised in Table 1.

Following APAP administration, MS/MS analysis of the various serum molecular forms of HMGB1 revealed a significant elevation in the necrosis-associated form at 3 hr post dose which peaked at 5 hr and returned to control levels by 20 hr. In contrast, a small but significant increase in the serum level of the immune cell derived form of HMGB1 could only be detected at 5 hr post dose. This level of this form increased over the time course, peaked at 15 hr and returned to control levels by 24 hr (FIG. 4A). A correlation of the level of full length against caspase-cleaved K18 present in serum following APAP administration shows the change from apoptotic to necrotic cell death over time (FIG. 4B).

To assess HMGB1 and K18 (full length and fragmented) as informative mechanism based biomarkers of APAP hepatotoxicity, receiver operator characteristic (ROC) analysis was undertaken in comparison with traditional serum indicators of hepatotoxicity (ALT). FIG. 4C demonstrates ROC curves and area under the curve analysis for serum fragmented K18 (0.84), full length K18 (0.90) and total HMGB1 (0.87) compared to ALT (0.80). Further validation of HMGB1 and K18 as biomarkers of DILI in these animal models was assessed by correlating individual animal serum HMGB1 and K18 levels with the degree of hepatocyte loss determined by histology (FIG. 5A-B) and the level of ALT activity. Increases in both serum full length K18 and HMGB1 correlated with an increase in the degree of hepatocyte loss. Correlation coefficients of $R^2=0.832$ and $R^2=0.746$ where obtained for K18 and HMGB1 respectively when correlated with the level of ALT activity following APAP administration (FIG. 5C-D).

Caspase Inhibition Increases APAP-Induced Necrosis

To confirm that K18 fragmentation was caspase dependent, mice were co-administered APAP with the caspase inhibitor Z-VAD.fmk. Z-VAD.fmk completely inhibited the detection of apoptotic markers in APAP dosed mice compared with APAP alone (FIG. 6A-C). Pre-treatment with either Z-VAD.fmk or the DMSO solvent control had no effect on APAP-mediated GSH depletion (FIG. 6D). However, Z-VAD.fmk and APAP administration resulted in increased serum ALT and serum HMGB1 levels compared with APAP alone (FIG. 6E-F). Histological scoring of centrilobular hepatocyte loss induced by APAP was generally 2-3 and therefore higher when APAP was co-dosed with Z-VAD.fmk ($p<0.05$) compared with APAP alone (FIG. 2.F). There was no evidence of apoptotic hepatocyte death by histology and immunohistology for cleaved caspease-3 (data not shown).

Discussion

Here we have used the mass spectrometry evaluation of differing molecular forms of HMGB1 and K18 in vivo as non-invasive and biologically informative biomarkers to further understand mechanisms leading to DILI.

APAP represents an important clinically relevant tool to explore mechanisms leading to 'off target' hepatotoxicity in animal models and to assess potentially useful hepatotoxicity biomarkers. Following histological and biochemical characterization, the hypothesis was tested that various mechanism and cell death model specific forms of HMGB1 and K18 could be identified and characterized in the sera of mice that were sensitive biomarkers of APAP hepatotoxicity.

Mass spectrometry provides unambiguous biomarker analyte identification and characterization to develop absolute and relative quantification methods across a wide range of pre-clinical test species. This has potential to aid bridging studies in drug safety analysis, clinical and basic research. The mass-spectrometric characterization of K18 present in mouse serum used in this investigation revealed that both full length K18 known to be released passively by necrosis and fragmented K18 released during apoptosis are released during APAP hepatotoxicity. MS/MS analysis showed that in the fragmented forms of K18 (DALD), and not the full length form (DALDSS), the caspase-cleavage motif was cut and exposed in a time dependent manner. This indicated that cleavage of caspase substrates does occur during APAP hepatotoxicity in this animal model. The data was consistent with the measurement of pro-caspase processing and DNA laddering. Moreover, MS analysis permitted the simultaneous analysis of elevations in the apoptosis and necrosis related K18 forms within the same sample. Correlations of individual animal full length and caspase-cleaved K18 levels reflected the histological progression and provided a non-invasive method to demonstrate apoptotic cell death within the first few hours post treatment, alongside necrotic cell death which was observed over the entire time period up to 24 hr post treatment. K18 quantifications suggested that necrosis was the major form of cell death at any time point. Histologically, apoptotic cells could be identified at earlier time points, and this was supported by the immunohistological demonstration of cleaved caspase-3 in cells with apoptotic morphology. Necrotic cells, however, were only rarely identified histologically, confirming that hepatocyte necrosis is a very rapid process which leads to cell loss already at a very early stage. However, by inhibition of caspase activation, significantly increased hepatic injury and complete abrogation of hepatocyte apoptosis was observed, as shown by increases in serum HMGB1, ALT activity and histology including cleaved caspase-3 immunohistology.

APAP-induced cleavage of K18 resulted in both a large 44 kDa fragment being produced from caspase 3, 7 and 9 cleavages and a smaller K18 fragment dependent upon the additional activity of caspase 6, rather than just the smaller fragment being produced. This Information could not be derived from current immunoassays which do not differentiate between the 44 and 21 kDa fragments. However, a 27 kDa fragment, derived from caspase 6 cleavage alone, could also be predicted but was not identified (16). A number of potential explanations account for this pattern of K18 cleavage. Activation of the intrinsic cell death pathway rather than the extrinsic pathway may account for the lesser involvement of caspase 6 (32, 33). Full activation of caspases would predict the smaller fragment being the predominant form. However, studies have indicated that the caspase 3, 7 and 9 site is cut prior to the caspase 6 site during optimal conditions (12). Due to the requirement of ATP for caspase activity (34) and the depletion of hepatic ATP with APAP hepatotoxicity the possibility exists that the decrease in hepatic ATP inhibits the caspase 6 mediated cleavage of K18 and a sustained apoptotic cascade and could provide an explanation for a mixture of both the large and small K18 fragment being produced.

MS/MS analysis identified both hypo-acetylated HMGB1, which is released from necrotic cells, and hyper-acetylated HMGB1, which is derived from activated immune cells, in the sera of APAP dosed mice. This information could not be derived from current immunoassays which do not different between differing molecular forms. Moreover, MS/MS analysis identified the acetylation of key lysine residues 180-185 within the nuclear localization sequence which has previously been identified as critical for the immune cell release of HMGB1 (24). During APAP hepatotoxicity, the molecular form derived from necrosis was significantly increased from 3 hr post treatment on, peaked at 10 hr and then dropped and was not detected any more at 20 hr. Interestingly, already at 15 hr post infection, there was no histological evidence of hepatocyte necrosis anymore and there was evidence of regeneration and induction of hepatocyte mitosis. The relatively short half-life of HMGB1 in serum and that its elevation followed by its decrease mirrored the hepatic cell loss and regeneration highlight an important feature of HMGB1 as a reflective biomarker of hepatic injury status. The immune cell derived form of HMGB1 was increased from 5 hr on, but to a far lower level, and until the end of the experiment at 24 hr. Interestingly, at no time point significant inflammatory cell infiltration was observed in the livers and only small numbers of neutrophils were seen centrilobularly in some animal between 5 and 15 hr post APAP. This indicates that necrotic hepatocyte death induced by APAP leads to immune cell activation and further supports the use of HMGB1 as a mechanism based biomarker of DILI. However, the exact role of HMGB1 during DILI and its origin from activated immune cells remain to be elucidated (35-38).

ROC curve analysis supported the time course evaluation that K18 and HMGB1 were more sensitive indicators of hepatotoxicity than ALT, although as predicted, serum ALT analysis was a more specific marker of hepatic damage. It is important to define dose and time points of correlations as well as discriminations to aid the potential utility of a safety biomarker. Further validation of K18 and HMGB1 as being mechanism based biomarkers of APAP hepatotoxicity was shown by strong correlations with increasing cell loss determined by histology and correlations with ALT activity. Although HMGB1 and K18 do not provide the same level of organ specificity as ALT activity, this data supports the hypothesis that HMGB1 and K18 provide sensitive and informative indicators of hepatic cell loss that can be used alongside ALT activity to provide enhanced mechanistic knowledge of DILI.

In summary, we have used mass spectrometry to identify and analyse the molecular forms of K18 and HMGB1 as mechanism based biomarkers linked to the development of APAP hepatotoxicity in a murine model. Such mechanism based serum biomarkers can be used in bridging studies between clinical, animals and in vitro systems to enhance our understanding of DILI in man and therefore provide strategies for its prevention.

Example 2

Detection of the Oxidised Form of HMGB-1

As stated above, caspase-dependent oxidation of the sulfhydryl group of C106 within the cytokine domain of HMGB-1 (FIG. 7A) is an important mechanism in neutralizing the inflammatory properties of HMGB-1 within apoptotic cells (39).

The applicant has found that the induction of the inflammatory response associated with paracetamol toxicity (in fasted animals) was associated with a lack of oxidized HMGB-1 in these animals compared to control animals (fed animals) which had received paracetamol also, but in which no toxicity was observed.

Western blot analysis of sera from fasted mice dosed with APAP displaying toxicity revealed that the only serum molecular form of HMGB-1 present was the reduced form (FIG. 7B). The predominant form of HMGB-1 in the sera of fed mice, which did not display toxicity, dosed with APAP was the oxidized, immune-tolerant form (FIG. 7B). Within the reduced HMGB-1 protein, a peptide of 1947.3 Da was characterized by MS/MS containing C106. Further MS/MS analysis identified peptides of 1963.3, 1979.3 and 1995.3 Da, only present in oxidized HMGB-1 and not the reduced form of HMGB-1. The progressive increase in 16 amu corresponded to the addition of oxygen to C106 to produce the sulfonic, sulfenic and sulfinic acid-containing residues (FIG. 7C-D). The caspase dependency of C106 oxidation was confirmed with the use of a pan-caspase inhibitor Z-VAD.fmk in APAP-treated, fed mice. This treatment resulted in only the reduced molecular form of HMGB1 being detected within these mice and associated with an increase in toxicity (FIG. B).

The immunostimulatory properties of HMGB1 have been found to vary depending on the oxidation status of the sulphydryl group on C106. Oxidation of this group is an intracellular post-translational modification and has been shown to be a caspase-directed process to promote immune tolerance (39). The applicant has demonstrated by western blot that the oxidized form of HMGB-1 is the predominant form in the blood of fed mice dosed APAP and was dependent upon caspase activation, this has only previously been observed in vitro (39).

TABLE 1

| Time point (hr) | Main histological features | In situ | | | | | Serum Biomarker elevation | | | |
|---|---|---|---|---|---|---|---|---|---|---|
| | | Cell loss score (average) | cleaved Caspase-3 (IH) | GSH depletion | DNA laddering | Caspase 3 processing (WB) | K18 (fragment) | K18 (full length) | Total HMGB1 | ALT activity |
| 3 | Centrilobular cell loss with numerous apoptotic cells mainly centrilobular | 1-2 | +++ | + | + | + | + | + | + | + |
| 5 | Centrilobular cell loss, variable numbers of apoptotic cells and increased number of necrotic cells, mainly centrilobular, increased numbers of mitotic hepatocytes. Space filled by erythrocytes (haemorrhage) | 1-3 (2) | −/+/++/+++ | + | + | + | + | + | + | + |
| 10 | Centrilobular cell loss, no or only scattered apoptotic cells mainly centrilobular; some increase in mitotic hepatocytes. | 1-2 | −/+ | − | − | + | + | + | + | + |

TABLE 1-continued

| Time point (hr) | Main histological features | In situ | | | | | Serum Biomarker elevation | | | |
|---|---|---|---|---|---|---|---|---|---|---|
| | | Cell loss score (average) | cleaved Caspase-3 (IH) | GSH depletion | DNA laddering | Caspase 3 processing (WB) | K18 (fragment) | K18 (full length) | Total HMGB1 | ALT activity |
| 15 | Centrilobular cell loss, but evidence of centrilobular cell replacement; numerous mitotic hepatocytes | 0-2 (1/2) | − | − | − | − | + | + | + | + |
| 20 | No evidence of or mild centrolobular cell loss; irregularly arranged centrilobular hepatocytes; numerous mitotic hepatocytes | 0-1 | − | − | − | − | + | + | − | + |
| 24 | No evidence of centrilobular hepatocyte loss; numerous mitotic hepatocytes | 0 | − | − | − | − | + | + | − | + |

REFERENCES

1. Pirmohamed M, James S, Meakin S, Green C, Scott A K, Walley T J, Farrar K, et al. Adverse drug reactions as cause of admission to hospital: prospective analysis of 18 820 patients.[see comment]. BMJ 2004; 329:15-19.
2. Ostapowicz G, Fontana R J, Schiodt F V, Larson A, Davern T J, Han S H, McCashland T M, et al. Results of a prospective study of acute liver failure at 17 tertiary care centers in the United States. Ann Intern Med 2002; 137:947-954.
3. Park B K, Kitteringham N R, Maggs J L, Pirmohamed M, Williams D P. The role of metabolic activation in drug-induced hepatotoxicity. Annu Rev Pharmacol Toxicol 2005; 45:177-202
4. Antoine D J, Williams D P, Park B K. Understanding the role of reactive metabolites in drug-induced hepatotoxicity: state of the science. Expert Opinion On Drug Metabolism & Toxicology 2008; 4:1415-1427.
5. Dahlin D C, Miwa G T, Lu A Y, Nelson S D. N-acetyl-p-benzoquinone imine: a cytochrome P-450-mediated oxidation product of acetaminophen. Proceedings of the National Academy of Sciences of the United States of America 1984; 81:1327-1331.
6. Kon K, Ikejima K, Okumura K, Aoyama T, Arai K, Takei Y, Lemasters J J, et al. Role of apoptosis in acetaminophen hepatotoxicity. Journal of Gastroenterology & Hepatology 2007; 22 Suppl 1:S49-52.
7. Kon K, Kim J S, Jaeschke H, Lemasters J J. Mitochondrial permeability transition in acetaminophen-induced necrosis and apoptosis of cultured mouse hepatocytes. Hepatology 2004; 40:1170-1179.
8. Ray S D, Jena N. A hepatotoxic dose of acetaminophen modulates expression of BCL-2, BCL-X(L), and BCL-X(S) during apoptotic and necrotic death of mouse liver cells in vivo.[erratum appears in Arch Toxicol 2000 March; 74(1):60]. Archives of Toxicology 2000; 73:594-606
9. Gujral J S, Knight T R, Farhood A, Bajt M L, Jaeschke H. Mode of cell death after acetaminophen overdose in mice: apoptosis or oncotic necrosis? Toxicological Sciences 2002; 67:322-328.
10. Gunawan B K, Liu Z X, Han D, Hanawa N, Gaarde W A, Kaplowitz N. c-Jun N-terminal kinase plays a major role in murine acetaminophen hepatotoxicity.[see comment]. Gastroenterology 2006; 131:165-178.
11. Knight T R, Jaeschke H. Acetaminophen-induced inhibition of Fas receptor-mediated liver cell apoptosis: mitochondrial dysfunction versus glutathione depletion. Toxicology & Applied Pharmacology 2002; 181:133-141.
12. Ku N O, Omary M B. Effect of mutation and phosphorylation of type I keratins on their caspase-mediated degradation. Journal of Biological Chemistry 2001; 276:26792-26798.
13. Caulin C, Salvesen G S, Oshima R G. Caspase cleavage of keratin 18 and reorganization of intermediate filaments during epithelial cell apoptosis. Journal of Cell Biology 1997; 138:1379-1394.
14. Schutte B, Henfling M, Kolgen W, Bouman M, Meex S, Leers M P, Nap M, et al. Keratin 8/18 breakdown and reorganization during apoptosis. Experimental Cell Research 2004; 297:11-26.
15. Cummings J, Ward T H, Greystoke A, Ranson M, Dive C. Biomarker method validation in anticancer drug development. British Journal of Pharmacology 2008; 153:646-656.
16. Tao G Z, Li D H, Zhou Q, Toivola D M, Strnad P, Sandesara N, Cheung R C, et al. Monitoring of epithelial cell caspase activation via detection of durable keratin fragment formation. Journal of Pathology 2008; 215:164-174.
17. Cummings J, Hodgkinson C, Odedra R, Sini P, Heaton S P, Mundt K E, Ward T H, et al. Preclinical evaluation of M30 and M65 ELISAs as biomarkers of drug induced tumor cell death and antitumor activity. Molecular Cancer Therapeutics 2008; 7:455-463.
18. Wieckowska A, Zein N N, Yerian L M, Lopez A R, McCullough A J, Feldstein A E. In vivo assessment of liver cell apoptosis as a novel biomarker of disease severity in nonalcoholic fatty liver disease. Hepatology 2006; 44:27-33.
19. Bantel H, Lugering A, Heidemann J, Volkmann X, Poremba C, Strassburg C P, Manns M P, et al. Detection of apoptotic caspase activation in sera from patients with chronic HCV infection is associated with fibrotic liver injury.[see comment]. Hepatology 2004; 40:1078-1087.
20. Kono H, Rock K L. How dying cells alert the immune system to danger. Nature Reviews. Immunology 2008; 8:279-289.
21. Scaffidi P, Misteli T, Bianchi M E. Release of chromatin protein HMGB1 by necrotic cells triggers inflammation. Nature 2002; 418:191-195.
22. Hon O, Brett J, Slattery T, Cao R, Zhang J, Chen J X, Nagashima M, et al. The receptor for advanced glycation end products (RAGE) is a cellular binding site for ampho terin. Mediation of neurite outgrowth and co-expression of rage and amphoterin in the developing nervous system. Journal of Biological Chemistry 1995; 270:25752-25761.
23. Park J S, Svetkauskaite D, He Q, Kim J Y, Strassheim D, Ishizaka A, Abraham E. Involvement of toll-like receptors 2 and 4 in cellular activation by high mobility group box 1 protein. Journal of Biological Chemistry 2004; 279:7370-7377.
24. Bonaldi T, Talamo F, Scaffidi P, Ferrera D, Porto A, Bachi A, Rubartelli A, et al. Monocytic cells hyperacetylate chromatin protein HMGB1 to redirect it towards secretion. EMBO Journal 2003; 22:5551-5560.
25. Wang H, Bloom O, Zhang M, Vishnubhakat J M, Ombrellino M, Che J, Frazier A, et al. HMG-1 as a late mediator of endotoxin lethality in mice. Science 1999; 285:248-251.
26. Jaeschke H. How relevant are neutrophils for acetaminophen hepatotoxicity?[comment]. Hepatology 2006; 43:1191-1194.
27. Masson M J, Carpenter L D, Graf M L, Pohl L R. Pathogenic Role of NKT and NK Cells in Acetaminophen-Induced Liver Injury is Dependent on the Presence of DMSO. Hepatology 2008; 48:889-897.
28. Goldring C E, Kitteringham N R, Elsby R, Randle L E, Clement Y N, Williams D P, McMahon M, et al. Activation of hepatic Nrf2 in vivo by acetaminophen in CD-1 mice. Hepatology 2004; 39:1267-1276.
29. Williams D P, Antoine D J, Butler P J, Jones R, Randle L, Payne A, Howard M, et al. The metabolism and toxicity of furosemide in the Wistar rat and CD-1 mouse: a chemical and biochemical definition of the toxicophore. Journal of Pharmacology & Experimental Therapeutics 2007; 322: 1208-1220.
30. Mercer A E, Maggs J L, Sun X M, Cohen G M, Chadwick J, O'Neill P M, Park B K. Evidence for the involvement of carbon-centered radicals in the induction of apoptotic cell death by artemisinin compounds. Journal of Biological Chemistry 2007; 282:9372-9382.
31. Jakob S, Corazza N, Diamantis E, Kappeler A, Brunner T. Detection of apoptosis in vivo using antibodies against caspase-induced neo-epitopes. Methods (Duluth) 2008; 44:255-261.
32. Budihardjo I, Oliver H, Lutter M, Luo X, Wang X. Biochemical pathways of caspase activation during apoptosis. Annual Review of Cell & Developmental Biology 1999; 15:269-290.
33. Cohen G M. Caspases: the executioners of apoptosis. Biochemical Journal 1997; 326:1-16.
34. Eguchi Y, Shimizu S, Tsujimoto Y. Intracellular ATP levels determine cell death fate by apoptosis or necrosis. Cancer Research 1997; 57:1835-1840.
35. Ishida Y, Kondo T, Kimura A, Tsuneyama K, Takayasu T, Mukaida N. Opposite roles of neutrophils and macrophages in the pathogenesis of acetaminophen-induced acute liver injury. European Journal of Immunology 2006; 36:1028-1038.
36. Ju C, Reilly T P, Bourdi M, Radonovich M F, Brady J N, George J W, Pohl L R. Protective role of Kupffer cells in acetaminophen-induced hepatic injury in mice. Chem Res Toxicol 2002; 15:1504-1513.
37. Liu Z X, Govindarajan S, Kaplowitz N. Innate immune system plays a critical role in determining the progression and severity of acetaminophen hepatotoxicity. Gastroenterology 2004; 127:1760-1774.
38. Liu Z X, Han D, Gunawan B, Kaplowitz N. Neutrophil depletion protects against murine acetaminophen hepatotoxicity.[see comment]. Hepatology 2006; 43:1220-1230.
39. Kazama H, Ricci J E, Herndon J M, Hoppe G, Green D R, Ferguson T A. Induction of immunological tolerance by apoptotic cells requires caspase-dependent oxidation of high-mobility group box-1 protein.[see comment]. Immunity 2008; 29:21-32.

The invention claimed is:

1. A method of detecting and/or assessing hepatic damage or injury associated with administration of a drug to a human or animal subject, the method comprising the steps of
   (a) testing a serum sample obtained from said subject for:
      (i) a specific serum biomarker of apoptosis;
      (ii) a specific serum biomarker of necrosis; and
      (iii) a specific serum biomarker of inflammation; and
   (b) correlating the presence of said serum biomarkers with a hepatic specific indicator of damage,
   wherein the serum biomarker of apoptosis is caspase-cleaved K18, the serum biomarker of necrosis is full length K18 and/or the hypoacetylated form of HMGB-1, and the serum biomarker of inflammation is the acetylated form of HMGB-1.

2. The method according to claim 1, wherein step (a) further comprises testing the serum sample for the presence of the oxidized form of HMGB-1.

3. The method according to claim 1, wherein the method further comprises
   (c) correlating the level of the serum biomarkers with predetermined levels to provide an indication of the severity of drug-induced hepatic damage or injury.

4. The method according to claim 3, wherein the predetermined levels are baseline levels obtained from the subject prior to the commencement of the administration of the drug.

5. The method according to claim 1, wherein the serum biomarkers of apoptosis, necrosis, and inflammation are detected by mass spectrometry.

6. The method according to claim 5, wherein serum K18 is partially digested with a protease enzyme to form fragments spanning the caspase cleavage motif prior to LC-MS/MS detection, wherein a fragment with the caspase cleavage motif intact corresponds to full length serum K18 and a fragment with the caspase cleavage motif cleaved corresponds to caspase cleaved serum K18.

7. The method according to claim 6, wherein the serum K18 is partially digested with trypsin to form full length K18 fragments spanning the DALD/S motif, wherein a fragment with the DALD/S motif intact corresponds to full length serum K18 and a fragment with the DALD/S motif cleaved corresponds to caspase cleaved serum K18.

8. The method according to claim 5, wherein serum HMGB-1 is partially digested with a protease enzyme to form HMGB-1 fragments comprising at least one lysine residue prior to LC-MS/MS detection, wherein a fragment in which the lysine residue is non-acetylated corresponds to hypoacetylated HMGB-1 and a fragment in which the lysine residue is acetylated corresponds to hyper-acetylated HMGB-1.

9. The method according to claim 8, wherein the serum HMGB-1 is partially digested with GLuC to form fragments comprising five lysine residues, wherein a fragment in which the lysine residues are non-acetylated correspond to hypoacetylated HMGB-1 and a fragment in which the lysine residues are acetylated corresponds to hyper-acetylated HMGB-1.

10. The method according to claim 1, wherein the serum biomarkers are detected by an immunologically based assay.

11. The method according to claim 1 wherein the hepatic damage or injury biomarker is selected from the group consisting of ALT (alanine aminotransferase), AST (aspartate aminotransaminase), AP (alkaline phosphatase), GLDH (glutamate dehydrogenase), and GGT (gamma-glutamyl transpeptidase).

12. An assay for detecting and/or assessing drug-induced organ or tissue damage, said assay comprising:
   means for detecting a specific serum biomarker of apoptosis;
   means for detecting a specific serum biomarker of necrosis; and
   means for detecting a specific serum biomarker of inflammation,
   wherein the serum biomarker of apoptosis is caspase-cleaved K18, the serum biomarker of necrosis is full length K18 and/or the hypoacetylated form of HMGB-1, and the serum biomarker of inflammation is the acetylated form of HMGB-1.

13. A kit for detecting and/or assessing drug induced hepatic damage or injury, said kit comprising:
   reagents for detecting caspase cleaved K18;
   reagents for detecting full length K18 and the hypoacetylated form of HMGB-1;
   reagents for detecting the hyper-acetylated form of HMGB-1.

14. The kit according to claim 13, wherein the kit further comprises reagents for detecting the presence of the oxidized form of HMGB-1.

* * * * *